(12) United States Patent
Washburn

(10) Patent No.: US 10,113,952 B2
(45) Date of Patent: Oct. 30, 2018

(54) COMBINED VIBRATIONAL SPECTROSCOPY AND LASER INDUCED BREAKDOWN SPECTROSCOPY FOR IMPROVED MINERALOGICAL AND GEOCHEMICAL CHARACTERIZATION OF PETROLEUM SOURCE OR RESERVOIR ROCKS

(71) Applicant: Ingrain, Inc., Houston, TX (US)

(72) Inventor: Kathryn Elizabeth Washburn, Houston, TX (US)

(73) Assignee: Ingrain, Inc., Houston, TX (US)

( * ) Notice: Subject to any disclaimer, the term of this patent is extended or adjusted under 35 U.S.C. 154(b) by 24 days.

(21) Appl. No.: 15/163,028

(22) Filed: May 24, 2016

(65) Prior Publication Data
US 2016/0349174 A1    Dec. 1, 2016

Related U.S. Application Data

(60) Provisional application No. 62/169,171, filed on Jun. 1, 2015.

(51) Int. Cl.
| | |
|---|---|
| *G01N 21/27* | (2006.01) |
| *G01N 21/71* | (2006.01) |
| *G01N 33/24* | (2006.01) |
| *G01N 29/46* | (2006.01) |
| *G01N 33/28* | (2006.01) |
| *G01N 21/3563* | (2014.01) |
| *G01N 29/12* | (2006.01) |
| *G01N 29/24* | (2006.01) |
| *G01N 30/88* | (2006.01) |

(52) U.S. Cl.
CPC ....... *G01N 21/272* (2013.01); *G01N 21/3563* (2013.01); *G01N 21/718* (2013.01); *G01N 29/12* (2013.01); *G01N 29/2418* (2013.01); *G01N 29/46* (2013.01); *G01N 33/24* (2013.01); *G01N 33/28* (2013.01); *G01N 2030/8854* (2013.01); *G01N 2291/0226* (2013.01)

(58) Field of Classification Search
CPC .. G01N 21/718; G01N 21/3563; G01N 21/35; G01N 33/24; G01N 33/28; G01N 2030/8854; E21B 49/00; E21B 49/005
See application file for complete search history.

(56) References Cited

U.S. PATENT DOCUMENTS

| | | | |
|---|---|---|---|
| 7,999,928 B2 * | 8/2011 | Beckstead | G01J 3/02 356/301 |
| 8,081,796 B2 | 12/2011 | Derzhi et al. | |
| 8,170,799 B2 | 5/2012 | Dvorkin et al. | |
| 2013/0270011 A1 * | 10/2013 | Akkurt | E21B 49/088 175/58 |
| 2015/0323516 A1 | 11/2015 | Washburn | |
| 2015/0323517 A1 | 11/2015 | Washburn | |

FOREIGN PATENT DOCUMENTS

| | | | |
|---|---|---|---|
| WO | 2004/003595 A1 | 1/2004 | |
| WO | 2013/023299 A1 | 2/2013 | |
| WO | 2013/071188 A1 | 5/2013 | |
| WO | WO-2014146719 A1 * | 9/2014 | G01J 3/443 |

OTHER PUBLICATIONS

Koujelev et al., "Artificial Neural Networks for Material Identification, Mineralogy and Analytical Geochemistry Based on Laser-Induced Breakdown Spectroscopy," Artificial Neural Networks—Industrial and Control Engineering Applications, Intech, Apr. 4, 2011, pp. 91-116.

Lalanne et al., "How to Cope with some of the Challenges Associated with Laboratory Measurements on Gas Shale Core Samples," SPE 167709, SPE/EAGE European Unconventional Conference and Exhibition, Vienna, Austria, Feb. 25-27, 2014 (17 pages).

Nordeng, "Evaluating Source Rock Maturity Using Multi-Sample Kinetic Parameters from the Bakken Formation (Miss.-Dev.), Williston Basin, ND," Geol. Investig. No. 164, North Dak. Geol. Survey, 2013, pp. 1-19.

Peters, "Guidelines for Evaluating Petroleum Source Rock Using Programmed Pyrolysis," The American Association of Petroleum Geologist Bulletin, V. 70, No. 3, Mar. 1986, pp. 318-329.

Bellucci et al., "A detailed geochemical investigation of post-nuclear detonation trinitite glass at high spatial resolution: Delineating anthropogenic vs. natural components," Chemical Geology 365, 2014, pp. 69-86.

Tiwari et al., "Detailed Kinetic Analysis of Oil Shale Pyrolysis TGA Data," AIChE Journal, Feb. 2012, vol. 58, No. 2, DOI 10.1002/aic, pp. 505-515.

Lalanne et al., "Benefits of High-Resolution Core Logs Integration in Characterizing Gas Shales Cores," International Symposium of the Society of Core Analysts, SCA Paper No. 2013-076, Sep. 2013, pp. 1-6.

Grader et al., "Computations of Porosity and Permeability of Sparic Carbonate Using Multi-Scale CT Images," International Symposium of the Society of Core Analysts, SCA2009-Temp Paper #03-10, Sep. 27-30, 2009, pp. 1-10.

* cited by examiner

*Primary Examiner* — Christopher Adam Hixson
(74) *Attorney, Agent, or Firm* — Chamberlain Hrdicka

(57) ABSTRACT

A method for determining mineralogical or geochemistry of at least one geological sample with vibrational spectroscopy combined with laser-induced breakdown spectral measurements performed on the geological sample in a time variant manner with spectral acquisitions made after each of a plurality of measurement shots, spectral pre-processing performed as necessary, and subsequent analysis is applied to the collected data to determine at least one mineralogical or geochemistry parameter of the sample. The method can provide a rapid method to estimate mineralogy or geochemical parameters of a sample, which does not require sample preparation, and which can be non-destructive with respect to portions of the sample. A system for performing the method also is provided.

15 Claims, 16 Drawing Sheets

COMBINED VIBRATIONAL SPECTROSCOPY AND LASER INDUCED BREAKDOWN SPECTROSCOPY FOR IMPROVED MINERALOGICAL AND GEOCHEMICAL CHARACTERIZATION OF PETROLEUM SOURCE OR RESERVOIR ROCKS

This application claims the benefit under 35 U.S.C. § 119(e) of prior U.S. Provisional Patent Application No. 62/169,171, filed Jun. 1, 2015, which is incorporated in its entirety by reference herein.

FIELD OF THE INVENTION

The present invention relates to a method for obtaining geochemistry and mineralogical information on geological samples or other types of samples and, more particularly, to a method for obtaining geochemistry and mineralogical information on geological materials with laser induced breakdown spectroscopy (LIBS) and vibrational spectroscopy methods. The present invention also relates to systems for the methods.

BACKGROUND OF THE INVENTION

Characterisation of source and reservoir rocks is important for evaluation of both conventional and unconventional reservoirs. In addition to inorganic matter, organic matter is deposited and preserved at the bottom of lakes, seas and deltas. As more material is deposited, the organic matter is buried and the heat and pressure of burial transforms the organic matter into geopolymers such as kerogen and bitumen. When the rocks containing organic matter are buried deep enough, the rocks undergo catagenesis, where temperature begins to convert the kerogen into bitumen and ultimately into hydrocarbons such as oil and gas. The rocks that produce hydrocarbons are referred to as source rocks.

Kerogen and bitumen are large organic molecules of no fixed structure. The composition of the kerogen and bitumen depends both on the type of organic matter used to produce them and the thermal maturity of the sample. While kerogen and bitumen have different molecular structures, they are typically separated functionally; the latter is soluble in common organic solvents while the former is not. The majority of bitumen is produced later during catagenesis, though a small amount occurs from diagenesis.

Understanding kerogen and bitumen properties and content is important for estimation of thermal maturity and potential hydrocarbon production. Thermal maturity indicates how much and what type of hydrocarbon is expected to be produced from an unconventional shale reservoir or a conventional reservoir sourced by a particular or multiple source rocks. In addition to kerogen and bitumen, a third class of organic matter, pyrobitumen, may exist in more thermally mature systems. Like kerogen, pyrobitumen is also insoluble in typical organic solvents. However, while kerogen originates from the originally deposited organic matter, the pyrobitumen comes from the cracking of bitumen during catagenesis and metagenesis.

The current standard method for determining thermal maturity is programmed pyrolysis, such as the "Rock-Eval™" (Vinci Technologies) or "Source Rock Analysis" techniques. These will heat up a crushed portion of sample in an oven or ovens in a series of stages at different temperatures to pyrolyse and oxidize the sample. The "Rock-Eval™" analyser, for example, includes a flame ionization detector (FID) that measures organic compound gases released during each stage of heating while sensitive infrared detectors are used to measure the quantity of CO and $CO_2$ generated during pyrolysis and oxidation of samples. A thermocouple monitors temperatures, which are recorded on a chart known as a pyrogram. The measured organic compound gases, CO and $CO_2$ are plotted as a function of temperature on the pyrogram. During the first heating stage, the sample is held at an initial temperature for a period of time and the produced products are measured. This is referred to as the S1 peak, which relates to the hydrocarbons and bitumen in the sample. The temperature is then ramped higher. A second peak, S2, corresponds to the hydrocarbons that evolve from the sample during the second programmed heating stage of pyrolysis, which result from the thermal cracking of kerogen. The associated release of carbon dioxide ($CO_2$) and carbon monoxide (CO) during pyrolysis is measured by the IR detector. The S3 peak corresponds to the amount of CO and $CO_2$ that is evolved from thermal cracking of the kerogen during pyrolysis. This peak is associated with the organic associated oxygen in the sample. The temperature at which the S2 peak has the highest signal intensity, and thus maximum generation of hydrocarbons from kerogen, is referred to as Tmax. Tmax relates to thermal maturity, as higher temperatures are required to crack the kerogen into hydrocarbons for more thermally mature samples. There is the potential to heat the sample up to even higher temperatures and observe the produced products. For example, the high temperature programmed pyrolysis can be used to measure the $S_{py}$ peak, which relates to pyrobitumen.

The programmed pyrolysis methods are bulk methods; the samples need to be crushed and homogenized before measurement. Therefore, any spatial information regarding the distribution of organic matter is lost during the crushing process. They are also, practically, completely destructive with respect to the samples, as the samples cannot be used for further tests after programmed pyrolysis. Programmed pyrolysis measurements are time intensive, usually requiring about an hour per sample to perform. The results also can have issues with interference from carbonate in the sample. If the samples are carbonate rich, they typically will need to be pretreated with hydrochloric acid to prevent interference in the measurement.

Thermal maturity is often estimated using the temperature where the maximum number of hydrocarbon products are produced from kerogen. This can be unreliable, as the Tmax peaks are often quite broad, such that the exact location of the peak can vary and can be difficult to reproduce with subsequent measurements. Thermal maturity calculations from Tmax are often unreliable particularly for low organic content samples. As programmed pyrolysis methods take approximately an hour per sample, this is a time intensive method to measure thermal maturity.

The standard method for obtaining mineralogical information is X-Ray diffraction (XRD). XRD works by irradiating samples with monochromatic x-rays, which are scattered at characteristic angles by crystalline materials. Amorphous materials, e.g. organic matter, contain no long term order and therefore will not produce peaks at characteristic angles. By observing the peak heights and location from a sample, the mineralogy of the sample can be estimated. This method is time consuming, requiring roughly half an hour measurement time depending on operation parameters. If clay speciation is required, the samples need to be treated with chemicals such as ethylene glycol and heated overnight, adding to the total time required. Further-more, XRD peaks are commonly assessed manually, which can lead to subjectivity and significant variation of results between operators.

Laser induced breakdown spectroscopy (LIBS) uses a laser to ablate a tiny portion of sample. The standard for LIBS uses a q-switched solid state laser that produces a rapid pulse, typically on the order of pico- to nanoseconds in duration. Optics are used to focus the energy onto a single spot on the sample and the laser is used to ablate a small portion of sample, creating a high temperature plasma. The excited atoms of the plasma then return to a ground state, giving off light at characteristic frequencies associated with different elements. The spot size vaporized by the laser can range in size from a few microns up to hundreds of microns, allowing a large range of resolution and is dependent on the optics of the system. The signal quality improves with larger spot size, but sacrifices resolution. While a small amount of sample is consumed, the amount is so small that it is considered to be negligible and the technique is considered non-destructive. The wavelength of light from the plasma can be in the 180 to 980 nm region. Detection means may comprise a spectrometer adjusted to a part of the spectral region. The resulting spectra can be analysed by multivariate data analysis to correlate the spectra to concentration of elements. The spectroscopic analysis of the optical emission in LIBS is different from analytical approaches based on mass spectrometry.

LIBS has been used as a method for mineralogy identification, making it an alternative to X-ray Diffraction (XRD) and X-ray Fluorescence (XRF) methods for mineralogical analysis of samples. It has an advantage over XRF for mineralogical identification because it can measure all elements, whereas XRF is unable to detect light elements. LIBS does have a disadvantage in terms of quantification of heavier elements compared to XRF.

LIBS has also been used previously to act as a rapid pyrolysis method to obtain TOC and geochemical parameters. The laser is used to both ablate material for measurement and to volatize organic material. By monitoring the changes in elements between laser shots, the rate and amount of loss of elements associated with organic matter (e.g. H, C) can be used to predict the geochemical properties of a sample.

Laser Induced Pyrolysis (LIPS) methods have been used previously on geological samples. LIPS relies on mass-spectroscopy methods of detecting and analysing the products of pyrolysis instead of optical emissions spectroscopy. Further, those LIPS methods appear to be limited to just total organic carbon (TOC), and do not appear to present information on thermal maturity or kerogen versus bitumen discrimination nor mineralogy.

Fourier transform infrared spectroscopy (FTIR) works by shining infrared light upon a sample and determining the wavelengths of light absorbed by the sample. The infrared region of the electromagnetic spectrum ranges from 700 nm to 1 mm and is broken up into the sub regions of: near infrared (0.7 to 1.4 µm), short wavelength infrared (1.4 to 3 µm), mid wavelength infrared (3 to 8 µm), long wavelength infrared (8 to 15 µm), and far-infrared (15 to 1000 µm). Molecular bonds in the sample have vibrational modes, (e.g. symmetrical and antisymmetrical stretching, rocking, wagging, scissoring, etc.) that can be excited by application of light at the same frequency as the vibrational mode. When the sample is irradiated with IR light, depending on the composition of the sample, some wavelengths of the light will be absorbed while others will pass through the sample. The transmitted light is then measured to produce a spectra showing the absorption profile as a function of wavelength. Organic matter and inorganic minerals have characteristic absorption profiles which can be used to identify sample constituents. This may be done qualitatively or quantitatively by use of mineral libraries, manual identification, univariate analysis or multivariate analysis. FTIR can be performed via transmission FTIR, diffuse reflectance infrared Fourier transform spectroscopy (DRIFTS), or attenuated total reflectance (ATR) FTIR.

Fourier Transform Infrared spectroscopy has been used to estimate both mineralogy and geochemical parameters. The exact minerals predicted varies between models, but typically consists of 5-10 different mineral species that are predicted. Analysis of the FTIR spectrum with multivariate analysis has shown good predictive value for geochemical parameters such as TOC, S1, S2, and to a lesser degree S3. Predictive ability of FTIR to date for hydrogen and oxygen indices and Tmax, however, has been of poor quality. Normal FTIR suffers the same drawback of loss of spatial resolution of the mineralogy and organic matter as XRD and programmed pyrolysis, as samples need to be powdered before measurement.

Fourier transform infrared (FTIR) microscopy combines FTIR measurements with spatial resolution to produce a FTIR spectrum. The FTIR microscope advances normal FTIR measurements by combining the technique with an optical microscope such that individual areas of a sample can be selected and FTIR spectra taken, allowing composition at a higher resolution to be determined. Unlike standard FTIR measurements which are normally performed on powders, the FTIR microscopy can be performed on intact samples. Standard procedure for geological FTIR microscopy uses a sample that is polished to produce an even surface. FTIR microscopy can be performed via transmission FTIR, diffuse reflectance infrared Fourier transform spectroscopy (DRIFTS), attenuated total reflectance (ATR) FTIR or photoacoustic FTIR spectroscopy.

Raman spectroscopy uses monochromatic light, usually from a laser, to excite rotational and vibrational modes in a sample. Raman spectroscopy measures the Raman scattering, the inelastic scattering that occurs when light interacts with matter. When photons from the laser interact with the molecular vibrations in the sample, they change the excitation state of the molecule. As the molecule returns to equilibrium, this results in the emission of an inelastically scattered photon that may be of higher or lower frequency than the excitation depending on whether the final vibration state of the molecule is higher or lower than the original state. These shifts give information on the vibrational and rotational modes of the sample, which can be related to its material composition. The signal to noise of Raman spectroscopy tends to be weaker compared to other methods such as FTIR.

Hyperspectral imaging creates a spectra for each pixel of an image. Light from an object passes through a dispersing element, such as a prism or a diffraction grating, and then travels to a detector. Optics are typically used in between the dispersing element and the detector to improve image quality and resolution. Hyperspectral imaging may range over a wide range of light wavelengths, including both visible and non-visible light. Multispectral is a subset of hyperspectral imaging that focuses on a few wavelengths of key interest. Hyperspectral imaging is defined by measuring narrow, well defined contiguous wavelengths. Multispectral imaging instead has broad resolution or the wavelengths to be measured are not adjacent to each other. Hyperspectral imaging has been used previously in a wide range of industries. In particular, hyperspectral imaging has been used in aerial mounted surveys to determine mineralogy for oil, gas, and mineral exploration.

Vibrational spectroscopy has the advantage that it is generally robust in prediction for larger categories of sample characterization (e.g. clays, carbonates. etc.), but often encounters problems in distinguishing subspecies. For example, carbonates such as calcite, dolomite, ankerite and siderite all have very similar FTIR absorption spectra. Clays also tend to have spectra that are similar to one another. Other minerals, like pyrite, lack a distinct FTIR spectrum, making prediction difficult of these minerals.

While LIBS works well to characterise samples similar to those used in the calibration set, it can encounter problems when trying to characterise samples in formations different than those used for calibration. Elements can belong to a wide variety of samples constituents and the elemental variations in minerals that occur in natural samples can make prediction on new samples challenging. In addition, samples of differing mineralogical structure may have similar elemental composition, which can make prediction more uncertain.

In the FTIR spectrum, the organic signal occurs as aliphatic and aromatic peaks. The aliphatic peaks in the spectra are usually well defined but the aromatic peaks overlap in the region of the spectra where the carbonate peaks occur. If there is a significant quantity of carbonate present, this makes it more difficult to distinguish the aromatic peaks. Multivariate methods such as partial least squares can be used to still predict organic content, but the results are more uncertain for more thermally mature samples, which predominantly have aromatic organic matter. Raman spectroscopy has problems with fluorescence from organic content that can interfere with spectral measurement of the samples.

With LIBS, while the hydrogen and carbon content of the organic matter is known, this ratio can vary with both the thermal maturity of the sample and the kerogen type, therefore making prediction of organic content and thermal maturity more uncertain.

Previous work has been done to combine Raman spectroscopy and LIBS measurements for development work for Mars Rover missions. These measurements have not been performed on petroleum source or reservoir rocks, but focused on rocks expected to be similar to those found on Mars, e.g., igneous materials.

SUMMARY OF THE INVENTION

A feature of the present invention is to provide an improved method for the analysis of a geological material.

A further feature of the present invention is a system for making such determinations.

To achieve these and other advantages and in accordance with the purposes of the present invention, as embodied and broadly described herein, the present invention relates, in part, to a method for determining mineralogy or geochemistry of a sample of a petroleum source or reservoir rock, comprising a) obtaining one set of spectral data comprising vibrational spectral data on at least one sample of a petroleum source or reservoir rock; b) obtaining another set of spectral data comprising LIBS spectral information on at least one sample of a petroleum source or reservoir rock; and c) obtaining at least one of mineralogical information or geochemical information on the at least one sample using the two sets of spectral data, wherein the sample in a) and the sample in b) are the same or are different but have the same or similar composition and structure. The vibrational spectroscopy measurement can comprise irradiating a sample with light of known wavelengths. Depending on the acquisition mode used, either the reflected or transmitted light from the sample can be measured using a spectrometer to determine the wavelengths absorbed by the sample. The LIBS measurement can comprise a plurality of successive measurement shots of laser light with each measurement shot at least partly vaporising and ionising the sample to cause spectral emission. The spectral emission can be detected after each measurement shot with at least one spectrum detector. The data from the vibrational spectroscopy and LIBS measurement may undergo optional or as necessary pre-processing of collected data from the spectrum detectors in order to transform the data into a suitable form for subsequent analysis before, analysis of the raw or preprocessed spectra and combining the data, and then determining at least one geochemistry or mineralogy parameter from the combined LIBS and vibrational spectroscopy data.

The present invention further relates to a method for determining mineralogy or geochemistry of a sample of a petroleum source or reservoir rock, comprising a) crushing a sample of a petroleum source or reservoir rock to form a powder thereof; b) mixing the powder to provide a homogenized sample; c) obtaining one set of spectral data comprising vibrational spectral data on a first portion of the homogenized sample; d) pressing another portion of the homogenized sample to provide a pelletized sample; e) obtaining another set of spectral data comprising LIBS spectral information on the pelletized sample; and f) obtaining at least one of mineralogical information or geochemical information on the sample using the two sets of spectral data.

The present invention further relates to a method for determining geochemistry of a sample of a petroleum source or reservoir rock sample, comprising a) obtaining one set of spectral data comprising vibrational spectral data on at least one sample of a petroleum source or reservoir rock; b) obtaining another set of spectral data comprising spectral information generated by laser induced pyrolysis on at least one sample of a petroleum source or reservoir rock; c) obtaining geochemical information on the at least one sample using the two sets of spectral data, wherein the geochemical information comprises kinetic analysis for at least one sample, wherein the sample in a) and the sample in b) are the same or are different but have the same or similar composition and structure; d) obtaining spatial information on the at least one sample; e) determining spatially resolved geochemical information for the at least one sample using the geochemical information and the spatial information.

The present invention further relates to a method for performing kinetic analysis as geochemical information of a sample of a petroleum source or reservoir rock, comprising a) making a vibrational spectroscopy measurement on at least one sample of a petroleum source or reservoir rock; b) heating at least one sample of a petroleum source or reservoir rock by laser-induced pyrolysis, wherein the sample in a) and the sample in b) are the same or are different but have the same or similar composition and structure; c) determining a reaction rate, such as a value of the Arrhenius equation rate constant k, of the at least one sample of b) comprising at least one of: i) determining changes in amounts of elements associated with organic matter and hydrocarbons for a portion of at least one sample that is heated by the laser-induced pyrolysis, ii) collecting and analysing hydrocarbon species produced by pyrolysis of a portion of at least one sample from the laser-induced pyrolysis by a flame ion detector or gas chromatography-mass spectrometry (GC-MS), iii) monitoring weight of at least one sample during the laser-induced pyrolysis of at least one sample, iv) monitoring the temperature of at least one sample and determining the amount of energy inputted into the portion of the sample by the laser during the laser-induced pyrolysis, or using any combination of i), ii), iii), and iv), such as ii) and/or iii) in conjunction with either i) or iv). The prefactor in the Arrhenius equation may be inputted based on a priori knowledge or solved for based on measurements performed on two or more different heating rates of the sample. The different heating rates may be obtained by one or more combinations of different laser power, laser spot size or laser shot rate. The kinetic analysis can be used to either solve for the activation energy distribution in the sample or the reaction rates given a known input of energy (e.g., inputted laser energy).

A system for performing these methods is also provided.

It is to be understood that both the foregoing general description and the following detailed description are exemplary and explanatory only and are intended to provide a further explanation of the present invention, as claimed.

The accompanying figures, which are incorporated in and constitute a part of this application, illustrate various features of the present invention and, together with the description, serve to explain the principles of the present invention. The features depicted in the figures are not necessarily drawn to scale. Similarly numbered elements in different figures represent similar components unless indicated otherwise.

DETAILED DESCRIPTION OF THE INVENTION

Figure 1:
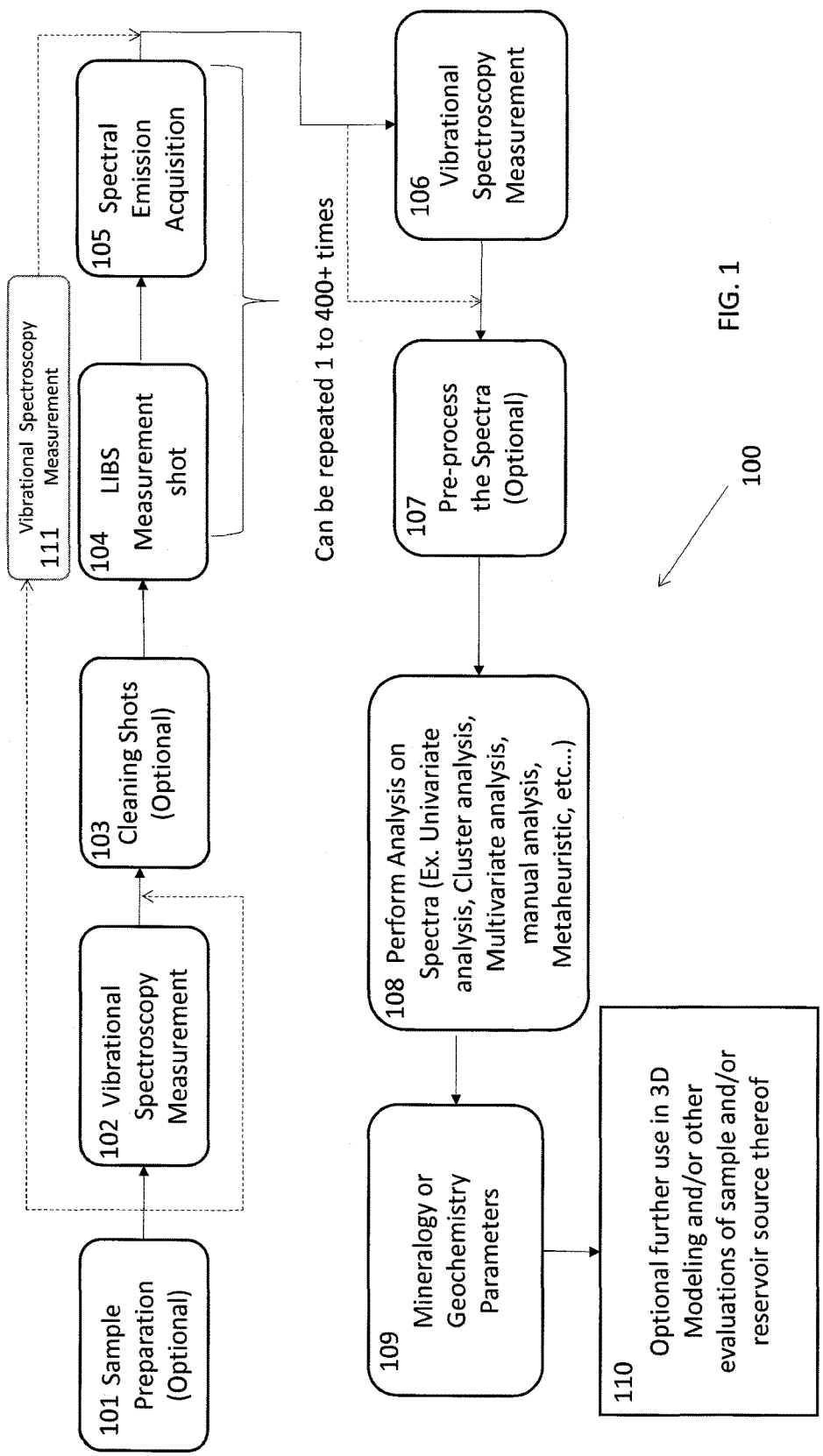
FIG. 1 shows a process flow chart of the determining mineralogy or geochemistry parameters for a sample according to an example of the present application.

The present invention relates in part to a method for determining geochemistry or mineralogy of at least one geological sample, such as petroleum source or reservoir rocks or other geological samples having organic content, with a combination of a vibrational spectroscopy technique and laser-induced breakdown spectral measurements. The vibrational spectroscopy measurement comprises irradiating a sample with light of known wavelengths. Depending on the acquisition mode used, either the reflected or transmitted light from the sample is measured using a spectrometer to determine the wavelengths absorbed by the sample. The LIBS measurement is performed on the geological sample in a time variant manner with spectral acquisitions made after each of a plurality of measurement shots. Optional or as needed pre-processing is applied to the collected vibrational spectroscopy and LIBS data from the spectral acquisitions and the raw or pre-processed data is analysed to determine at least one mineralogy or geochemistry parameter of the sample. Though the present invention is illustrated herein with regard to analyses of geological samples which are petroleum source or reservoir rocks or other geological samples having organic content, it will be appreciated that the invention may have broader application, such as in metallurgy, mineral prospecting, or other uses.

More specifically, in obtaining spectral data of a sample for the LIBS measurements according to a method of the present invention, after cleaning shots, multiple shots of a laser can be performed in rapid succession on the sample to pyrolyse organic matter, wherein a spectral measurement can be taken after each laser pulse, and observation of the loss of elements associated with organic material, typically but not limited to hydrogen, oxygen and carbon, can be observed as the number of laser shots increases.

The collected data from the vibrational spectral or LIBS measurements, or both, can be pre-processed in order to make the raw data suitable for subsequent analysis to produce one or more minerals or geochemical parameters. Pre-processing is a way to take raw data and make it suitable for analysis. For example, pre-processing can be performed by integration of a LIBS peak area associated with a given element to produce an intensity curve for the element as a function of laser shot number. This can be performed for one or more peaks, either associated with the same element or different elements. The preprocessing can also comprise, for example, analysing the peak maxima associated with an element to produce an intensity curve with laser shot number for one or more elements, sub-selecting actual peak spectra for successive measurement shots, or sub-regions of the spectra or the whole spectra for the successive measurement shots, or compiling the data from the successive laser shots into a matrix, single vector, or other combined form. Preprocessing may include normalization or baseline correction of either the LIBS or vibrational spectral data. Pre-processing of vibrational spectroscopy data may include integration of peak areas associated with given minerals or organic matter. This can be performed for one or more peaks, either associated with the same constituent or different constituents. Pre-processing may also include, but not limited to applying an exponential fitting, bi-exponential fitting, multiple-exponential fitting, an inverse Laplace transform, a Gaussian decay fitting, or other analysis or filter or function to the data, such as taking a derivative, or removing data that do not meet quality control standards. Pre-processing may include a combination of any two or more of these listed steps. Uni-, cluster, multi-variate analysis, neutral nets, self-organising maps, metaheuristic procedures (e.g. particle swarm optimization, genetic algorithms, etc.) or manual analysis can be applied to raw or pre-processed data to produce mineral or geochemistry parameters.

Figure 2:
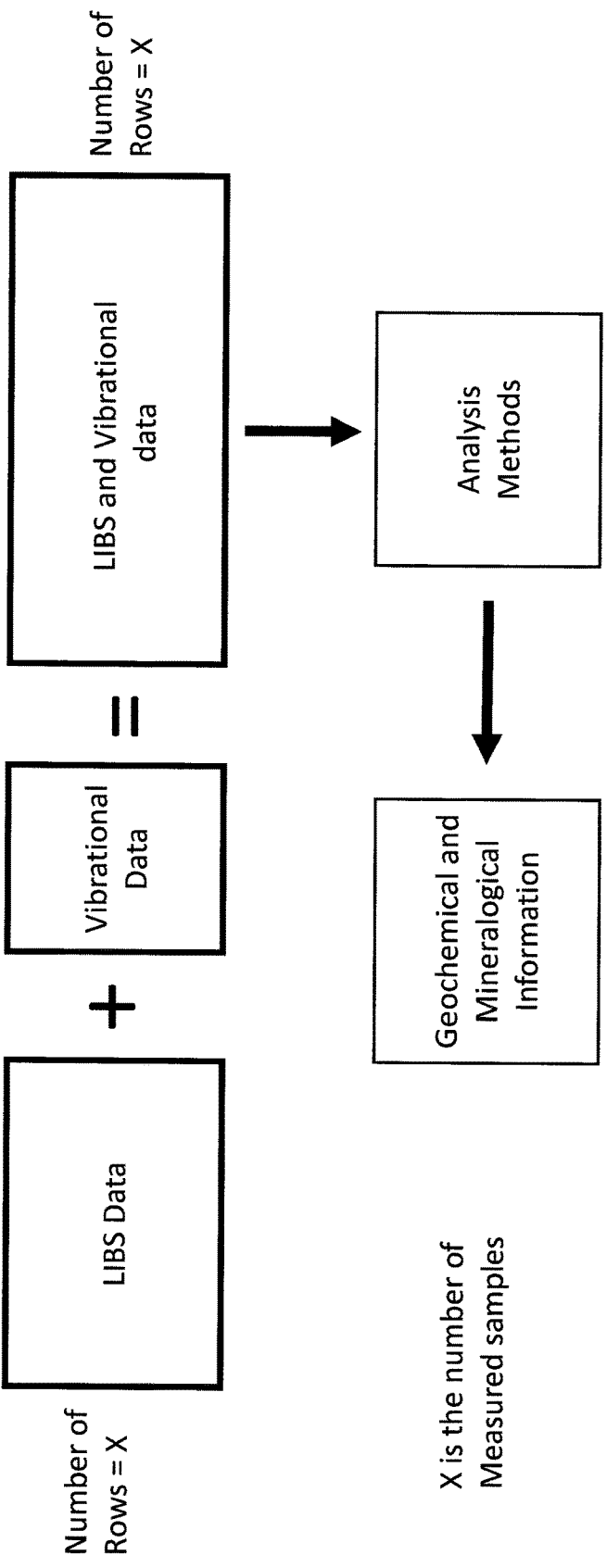
FIG. 2 shows a method of combining vibrational spectroscopy and LIBS data for prediction of mineralogical or geochemical analysis according to an example of the present application.
Figure 3:
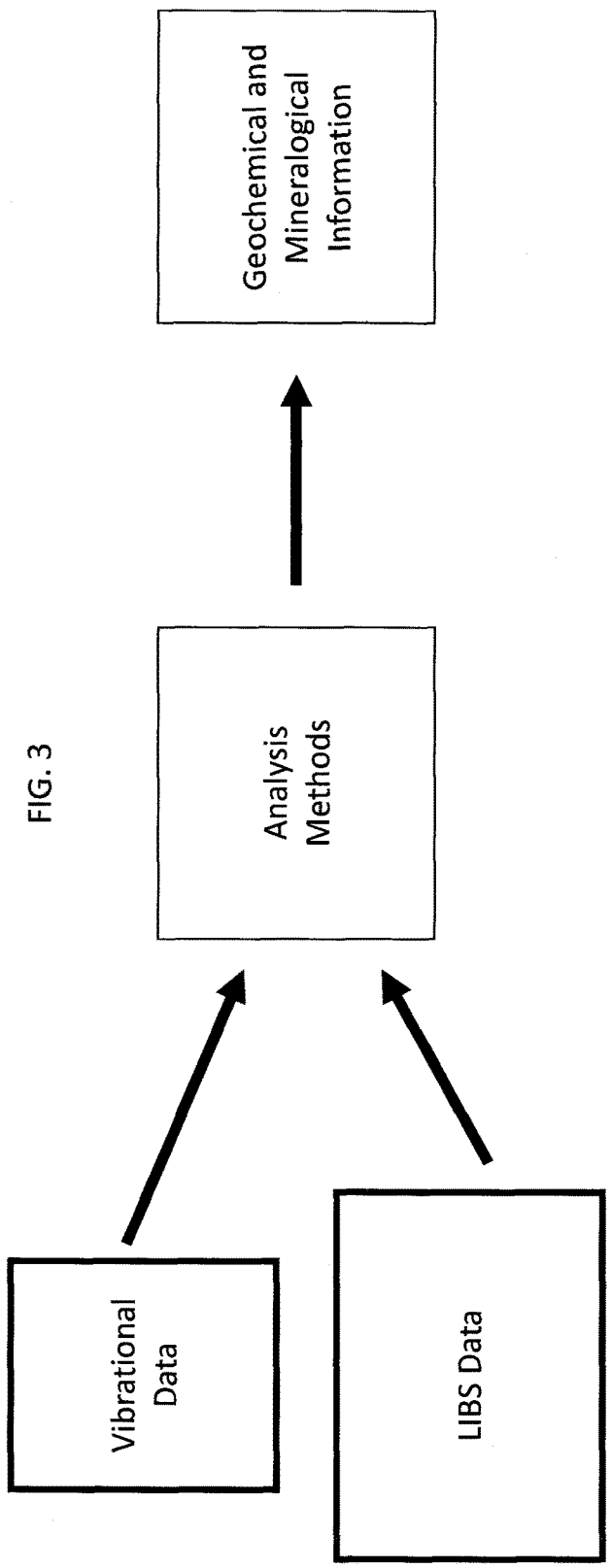
FIG. 3 shows a method of combining vibrational spectroscopy and LIBS data for prediction of mineralogical or geochemical analysis according to an example of the present application.
Figure 4:
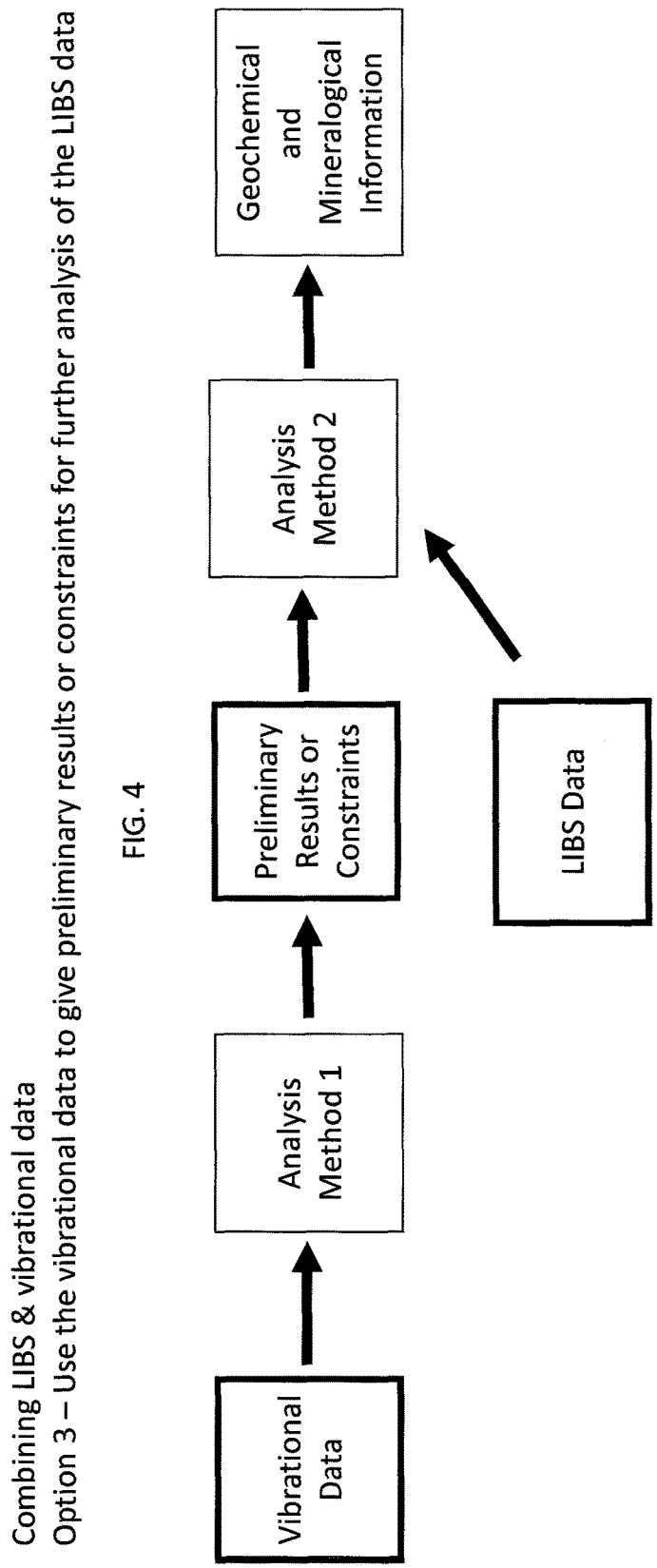
FIG. 4 shows a method of combining vibrational spectroscopy and LIBS data for prediction of mineralogical or geochemical analysis according to an example of the present application.
Figure 5:
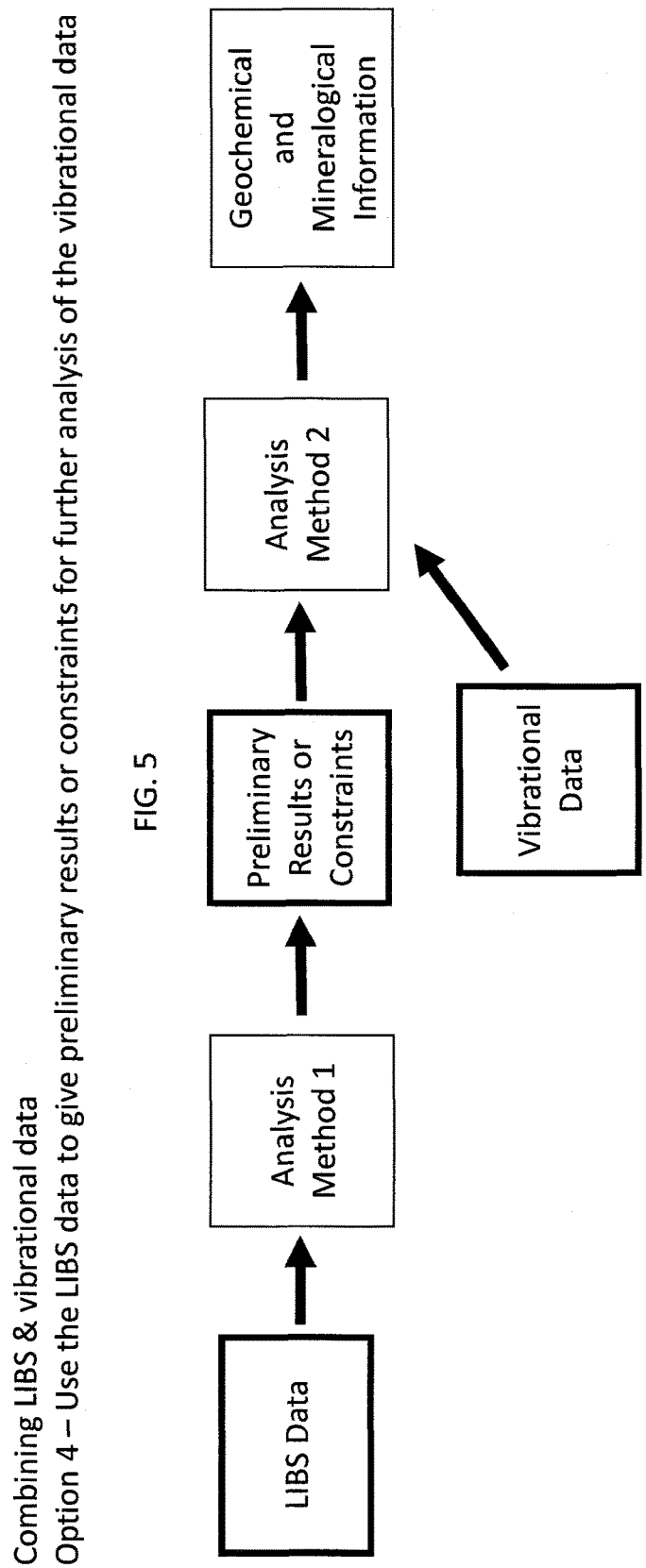
FIG. 5 shows a method of combining vibrational spectroscopy and LIBS data for prediction of mineralogical or geochemical analysis according to an example of the present application.

The vibrational spectroscopy and LIBS data can be combined for analysis in several manners. The simplest method is to concatenate the data, turning the two or more separate data matrices into a single matrix that contains both the vibrational spectroscopy and LIBS data. This combined matrix can then be used in the analysis methods to predict mineralogy and geological parameters. This method is illustrated in FIG. 2 (Option 1). Other more advanced methods may involve inputting the one or more vibrational spectroscopy measurements and LIBS data separately into the analysis method, such as the Multi-Block or N-PLS method, for prediction of mineralogical and geochemistry parameters. This method is illustrated in FIG. 3 (Option 2). Another method of combining the data involves initially analyzing the vibrational spectroscopy data to get out initial predictions or constraints on mineralogical or geochemical parameters that are then inputted with the LIBS data for subsequent analysis. The initial predictions or constraints from the vibrational spectroscopy may either be inputted as a separate matrix into the second analysis method or may be concatenated with the LIBS data to create a single, large matrix. This method is illustrated in FIG. 4 (Option 3). Similarly, combining the data can also involve initially analyzing the LIBS data to get out initial predictions or constraints on mineralogical or geochemical parameters that are then inputted with the vibrational spectroscopy data for subsequent analysis. The initial predictions or constraints from the LIBS may either be inputted as a separate matrix into the second analysis method or may be concatenated with the vibrational data to create a single, large matrix. This method is illustrated in FIG. 5 (Option 4).

Combination of the vibrational spectroscopy with the LIBS data takes advantage of the strength of both techniques to help overcome the limitations of the two techniques separately. The vibrational spectroscopy helps provide the broad categories of the sample constituents and limiting the possible solution space of LIBS predictions, helping solve the issue of resolving samples of similar elemental composition but different mineralogy. The LIBS data provides the elemental sensitivity to discriminate subspecies where vibrational spectroscopy often has very similar spectra. For geochemistry, the distinct peaks of organic matter in vibrational spectroscopy help predict the total organic content of a sample, which then helps improve prediction of sample thermal maturity and kerogen quality based on the H/C ratios from the LIBS data.

The method of the present invention can provide a rapid method to estimate thermal maturity of a sample, such as rapid thermal maturity estimates which can be translated along the length of a core. A more complete elemental set can be provided using the method of the present invention than XRF, with decreased sample preparation time being needed. The vibrational spectroscopic data can help provide constraints on the elemental data, improving the predictions. The method can be non-destructive with respect to most portions of the sample other than the small spot or spots where the laser was impinged. A system for performing the method also is provided.

Further, the mineralogy or geochemistry parameter or parameters determined from the vibrational spectroscopy and LIBS measurements of the method of the present invention can be used as an input parameter or parameters for use in further source or reservoir rock evaluation. The mineralogy or geochemistry parameter or parameters obtained with the present method can be used for three-dimensional analysis of the geological sample. For example, the mineralogy or geochemistry parameters determined by the vibrational spectroscopy and LIBS measurements can be integrated with spatial information obtained on the same sample to produce three-dimensional models of the mineralogy or geochemistry of the geological sample. The method can allow for kerogen and bitumen to be distinguished in the samples. Spatially resolved maps, for example, can be obtained with the method of the present invention which can be applied to sample models to help distinguish between kerogen and bitumen in the models. Spatially resolved geochemical information can be obtained on the sample by integrating the geochemistry parameters obtained from the indicated vibrational spectroscopy and LIBS measurements with spatial information obtained on the sample. As another example, the geochemistry parameters determined by the vibration spectroscopy and LIBS measurements of the inventive method can be integrated with properties measured by other analytical techniques, such as TOC, S1, S2, S3, $T_{max}$, Ro, HI (hydrogen index), OI (oxygen index), kerogen typing, organic sulphur content, trace element analysis, or other properties determined from programmed pyrolysis, and/or from other methods, for further evaluation or modeling of the sample. Spatially resolved mineralogical information can be obtained on the sample by integrating the mineralogical parameters obtained from the indicated vibrational spectroscopy and LIBS measurements with spatial information obtained on the sample.

FIG. 1 shows a process flow of a method according to an example of the present invention. The method is shown in the figure as process (100), which can include steps 101-111. The sequence of the steps is indicated by the arrows in the figure, and several of the steps can be optional. The method steps are shown as including sample preparation (optional or as needed), vibrational spectroscopy measurements (either before or after the LIBS measurement or both), cleaning shots (optional or as needed), measurement shot, spectral acquisition, spectral pre-processing (optional or as needed), manual or uni- or cluster or multivariate analysis or neural net or self-organising maps or metaheuristic procedures (e.g. particle swarm optimization, genetic algorithms, etc.) for mineralogical and geochemical parameters attainment, and optional further use of mineralogical and geochemical parameters obtained in further modeling of the geochemistry or characteristics of the sample and/or geological reservoir from which the sample was obtained. As indicated, vibrational spectroscopy measurements can be taken before (102), after (106), or at the same time (111), as the LIBS measurement (104), or in combinations of steps 102, 106, and 111 (e.g., in steps 102 and 106). The possible methods of combining the vibrational spectroscopy data and LIBS data for the data analysis are shown in FIG. 2-5. Additional details on these various method steps are proved in the descriptions below with further reference made to this and other figures.

The materials, also referred to herein as the samples, to which the present invention can be applied are not necessarily limited. The materials can be geological materials, such as rocks, or samples or subsamples thereof. The kinds of rock to which a method of the present invention can be applied are not necessarily limited. The rock sample can be, for example, organic mud rock, shale, carbonate, sandstone, limestone, dolostone, or other rocks, or any combinations thereof, or other kinds. The rocks can be porous or non-porous. Any source of a rock formation sample of manageable physical size and shape may be used with the present invention. Micro-cores, crushed or broken core pieces, drill cuttings, sidewall cores, outcrop quarrying, whole intact rocks, and the like, may provide suitable rock piece or fragment samples for analysis using methods according to the invention.

FTIR measurements are able to be performed in a variety of setups. The oldest FTIR method used is the transmission method. The transmission FTIR method is also considered to be the most accurate way of performing FTIR measurements. Samples are crushed into a fine powder and diluted with a FTIR invisible material, such as KBr. This is done in order to get the concentration of sample to be measured down to a level where Beer's law is valid for relating the absorption of the infrared light to concentration. After dilution, the samples are turned into pellets. This can be done by pressing powder into self-supporting cylindrical shapes. This can be a time consuming process and care must be taken as pellets are prone to cloudiness and cracking, which can adversely affect the FTIR results. Once pelletization is complete, the samples can be placed in the FTIR equipment. Infrared light is then shined upon the pellets. The light transmitted through the sample is measured and used to determine the intensity and wavelengths of the absorbed light. Another acquisition mode is the diffuse reflectance mode (DRIFTS). This method requires the samples to be crushed. In order to avoid distortions to the spectra from grain effects, the samples need to be pulverized to a uniform grain size under 5 µm. For best results, the samples should be diluted with KBr or a similar material, though sometimes measurements are made upon the neat samples. IR light is then shined upon the samples. Some of the light will be transmitted through the sample, certain wavelengths of the IR light absorbed depending on the sample make up, and then reflected back to the detector. The reflected light is measured at an angle to the sample to avoid measurement of light that is directly reflected by the sample without transmission through the sample. There is no physical contact made with the sample, making the method amenable to automation. Another acquisition mode is attenuated total reflectance. ATR-FTIR has less exacting sample preparation than the other two methods. The samples need to be crushed but do not have the rigid limitations on grain uniformity and size that DRIFTS samples have. Measurements via ATR-FTIR do not need to dilute the sample with KBr or a similar materials and can be made upon neat sample. The sample is placed on the internal reflection element, typically a diamond or germanium crystal, and then pressure is applied to the sample using an anvil. IR light is passed through the crystal so that it will reflect at least once with the internal surface of the sample. The light is measured as it exits the crystal in order to determine the intensities and wavelengths of light that have been absorbed. Standard ATR-FTIR methods are not conducive for automation due to the need to manually place the sample on the internal reflection element, lower and raise the anvil, and then clean the sample from the sample stage.

More recent developments are the use of the FTIR microscope to perform mineralogy and geochemistry analysis. Instead of crushing the sample, this acquisition mode is able to be performed non-destructively. This allows spatially resolved measurements as well as retaining information on sample heterogeneity that is lost when samples are crushed and homogenized for traditional FTIR measurements. Measurement generally only penetrates to a 0.5-2 micron depth in the sample. FTIR-Microscopy measurements are typically performed in either the DRIFTS or ATR acquisition mode. ATR is frequently preferred as the DRIFTS mode requires the sample surface to be polished in order to obtain high quality spectra, though the quality of the spectra still tend to be worse than the spectra obtained using ATR. The DRIFTS mode may be preferred if physical contact with the sample may alter or damage the surface. For ATR acquisition via FTIR-microscopy, the anvil lowering and raising is controlled automatically by the acquisition software. Therefore, multiple measurements can be made without the need for operator to control each measurement, making the technique amenable for automation. FTIR-Microscopy is also able to be performed in transmission mode but is less commonly used.

Figure 7:
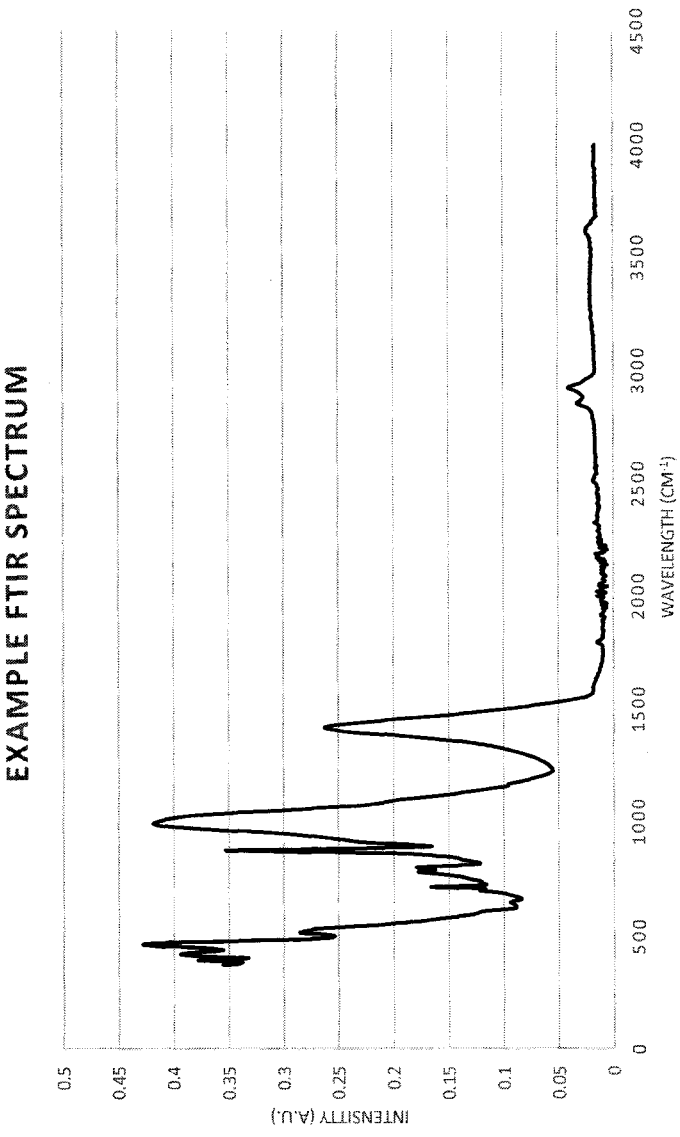
FIG. 7 shows an example of a FTIR spectrum according to an example of the present application.

Measurements illustrated herein were performed on a Bruker TENSOR spectrometer (Bruker Corporation) using a Pike Attenuated Total Reflectance-FTIR (ATR-FTIR) accessory (Pike Technologies). The accessory monitors pressure applied to the sample and measurements were performed at approximately 350 N applied pressure. Measurement was taken with 1880 points at a resolution of 4 $cm^{-1}$ over the wavelengths from 4000 to 375 $cm^{-1}$. 16 scans were measured and averaged together to improve signal to noise of the sample. An example of a FTIR spectrum obtained with the equipment is shown FIG. 7.

The FTIR spectra were area normalized before analysis, but no other pre-processing was performed here. In some cases, baseline correction of the results may help improve results of analysis. The entire FTIR spectra was used here for analysis but only select regions associated with certain minerals or organic matter species may also be used in analysis.

LIBS is able to perform depth profiling, firing or pulsing the laser in the same spot and observing the different products that are produced with increased depth. LIBS is also very rapid, only taking seconds per measurement making it amenable for high-throughput industrial use. LIBS measurements can be rastered to produce a two dimensional map of surface composition. When a LIBS measurement is performed on a sample, the laser produces heat that is transferred to the matrix surrounding the shot point. The energy transfer is dependent on the power of the laser, duration of the laser pulse, repetition rate of the laser and the laser spot size. The transfer of energy can lead to volitisation of organic components in the sample in the matrix nearby the laser shot. This loss of organic matter is then detected in the next LIBS measurement. Some components volatise more easily than others. Hydrocarbons and bitumens appear to volatise more rapidly than kerogen, which require more shots of the laser before its loss is detected. Less thermally mature kerogen appears to volatise more easily than more thermally mature kerogen. This is analogous to the programmed pyrolysis measurements, where the kerogen requires higher temperatures than hydrocarbons and bitumens for volitisation and more thermally mature kerogen requires higher temperatures than the immature kerogen.

LIBS is normally performed in a time invariant manner. Frequently a few cleaning shots with the laser are performed in order to remove any unwanted surface contamination. Information from these cleaning shots typically is not saved, but may be. After any cleaning shots, the actual measurements are performed; the laser is used to ablate the sample and the resulting spectral emissions from the produced plasma are recorded. Usually multiple shots are performed. Because there is usually not expected to be any significant changes in the sample with each individual laser shot, the spectral results are commonly added together to improve signal to noise. Other times, each individual spectrum from each laser shot may be recorded, for example if there are expected changes in composition with sample depth. Multiple points on the same sample are frequently sampled in order to confirm repeatability, assess homogeneity and identify any unusual results.

In contrast, LIBS measurements in a method of the present invention are performed in a time variant manner. Unlike LIBS measurements done in a time invariant manner, the time between laser shots is important for the thermal transfer to the surrounding matrix. Low level cleaning shots may be performed in order to remove surface imperfections or contaminants, but a weak power setting typically is used for the cleaning shots in order to avoid pyrolysation of the nearby organic matter. After any cleaning shots, multiple shots of the laser are performed in rapid succession to pyrolyse organic matter. Because a spectral measurement is taken after each laser pulse, observation of the loss of the elements associated with organic material, typically but not limited to hydrogen, oxygen and carbon, can be observed as the number of laser shots increases. The spectral measurement can be based on intensity for a selected spectrum region, or other parameters that can be correlated to elemental content of the sample. Averaging of multiple shots is less likely to be helpful than normal LIBS done in a time invariant manner because of the change in composition with each laser shot. Averaging the signal from measurements at multiple points on the sample may be useful to improve signal to noise and average out heterogeneity in the sample. The total signal loss may be related to the amount of organic matter in the sample and the rate of loss of organic matter to the sample thermal maturity.

Figure 8:
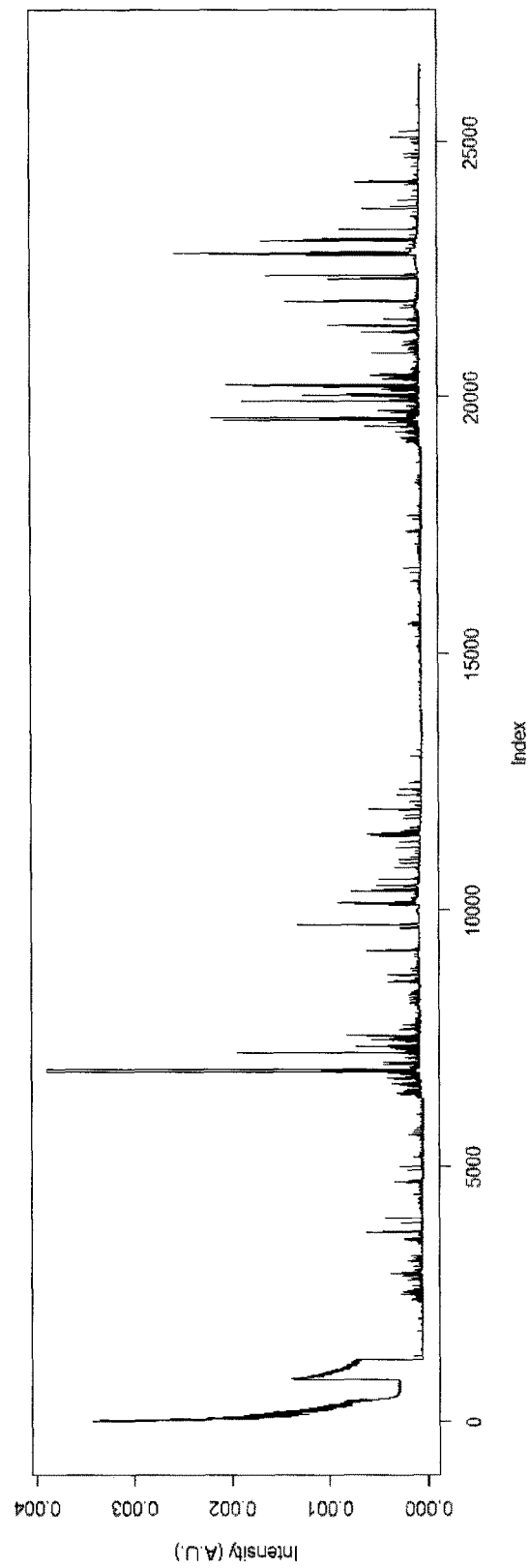
FIG. 8 shows an example of LIBS data for a sample where the H, C, and O decay curves have been concatenated with a LIBS spectrum from the start of measurement and a LIBS spectrum from the end of measurement according to an example of the present application.

Results for samples that had LIBS spectral acquisition measurements determined for them according to a method of the present invention that are shown in the some of the figures described herein, such as in FIG. 8. The initial 3 curves are created by integration of the hydrogen, carbon and oxygen peaks respectively. However, more advanced analysis on one or more other peaks, partial spectra or whole spectra for each, or a subset, of the laser shots may be used to give other information on thermal maturity, kerogen/bitumen discrimination and organic matter typing. Samples not containing significant quantities of organic matter usually show a stable behaviour of the hydrogen peak. Certain settings of the laser size, power, duration and repetition rate can be optimal for characterizing some samples while other types of samples will have different setting requirements for optimal characterisation. Thermally mature samples show longer decay curves. Conversely, observing the increase of the elements associated with inorganic material in organic rich samples may also yield information on sample properties. Unlike typical LIBS measurements, which are considered non-destructive, considerable sample alteration may occur near the point of laser ablation.

Figure 6:
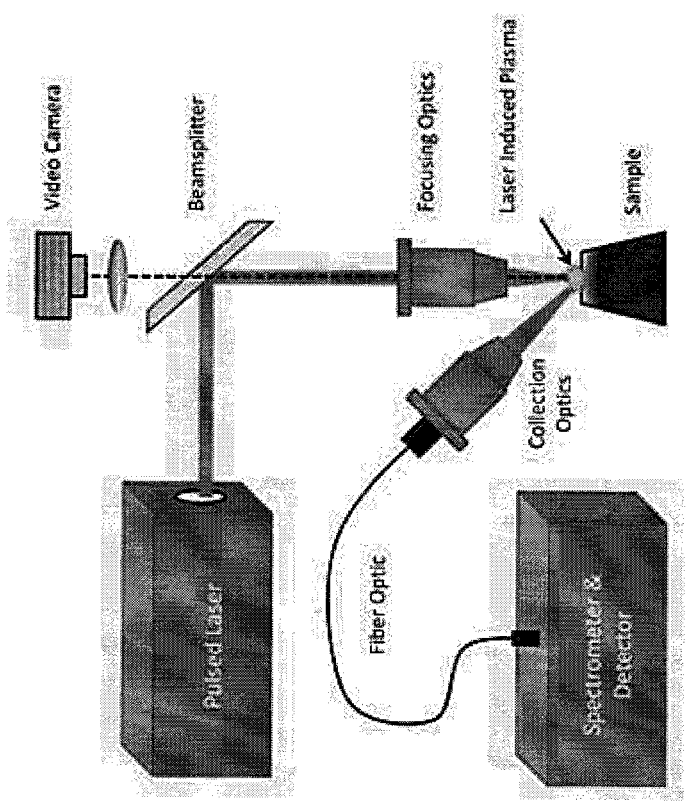
FIG. 6 shows an example setup of laser induced breakdown spectroscopy equipment according to an example of the present application.

In accordance with the practice of examples of the present invention, a LIBS analyzer that has the configuration shown in FIG. 6 was used. The LIBS analyzer used was commercially obtained from TSI Incorporated. The measurements were performed on the company's (TSI) latest model of LIBS analyzer and has the name ChemReveal. Measurements were made using a 250 mJ laser operating at 36% power. Shot rate was 5 Hz and laser duration was 200 microseconds ($\mu$s). Laser spot size on the sample was 400 micrometers ($\mu$m). Samples were placed on a three axis adjustable stage. A high-resolution camera was used to adjust the sample stage to the correct distance for measurement and see where on the sample the laser would be fired. Argon was flowed over the sample during measurement to avoid unwanted influence of elements commonly present in air (H, N, O, etc.) in the measurement. 400 shots of the laser, including acquisition of the light spectra after each laser shot, were measured. This appears to be adequate for most samples, though it appears more shots may be required for some of the very organic rich or very thermally mature samples to reach an equilibrium.

Optionally, one or more cleaning shots can be made on the sample before the LIBS or vibrational spectral measurement. The sample may be subjected to cleaning shots as-is without the need for any additional previous or subsequent sample preparation before the sample is subjected to the measurement shots. As indicated, cleaning shots may be performed in order to remove surface imperfections or contaminants, but a weak power setting typically is used for the cleaning shots in order to avoid pyrolysation of the nearby organic matter. In the measurement shots, the LIBS spot focus can be solely on organic matter of the sample, or the spot can focus on both organic and inorganic matter and the contribution of the organic matter is deconvoluted through manual or uni or multivariate analysis or cluster analysis or self-organising maps or neural nets or meta-heuristic procedures (e.g. particle swarm optimization, genetic algorithms, etc.). A single LIBS measurement or multiple LIBS spectral measurements can be used for the geochemical analysis.

In LIBS, the light emitted from the plasma as it cools is measured. The measured light is usually in the wavelength range of 180 to 900 nm. Intensity peaks for different elements can be plotted as intensity (arb. units) versus wavelength (nm). Certain elements will have peaks located at distinctive wavelengths. Sometimes there exists multiple peaks for a given element, though frequently one peak of an element is more desirable for analysis (e.g. stronger intensity, fewer nearby peaks that could interfere) than other peaks produced by that element.

The method of pre-processing the data can involve integrating the intensity for a given peak. Because there may be intensity changes in the spectra depending on the exact volume of sample ablated, the whole spectrum was normalized at the start of pre-processing. This was performed by dividing the entire spectrum by the total signal intensity (the summation) of the spectrum. There are other possible ways of normalizing (e.g. normalizing to a strong peak), but this appeared to be the best way to normalize. This was then repeated on the spectrum from the next laser shot on a given sample until all the spectra from all the laser shots had been normalized.

After the spectra were all normalized, the intensity of each of a desired peak relating to a particular element was integrated. Because the peaks have finite width, in order to capture the complete intensity, three points on either side of the center of the peak were also included in the integration and the value recorded. This is repeated for the next shot number until the intensity for the peak for each shot of the laser has been determined. The integrated intensity of the peak is then combined into a vector, which may be plotted visually to aid in understanding the changes in the element with shot number. This vector then shows how the intensity, and thus the concentration, of the element changed with each firing of the laser. This may be repeated for other peaks, either different peaks of the same element, or peaks relating to other elements to produce vectors relating to how each of those elements decay. Because some elements produce stronger peaks than others, direct comparison of intensities versus one another does not appear possible, though some conversion factors may exist that may make that possible. The peaks used for the analysis in this example were the H peak located at 656 nm, the C peak at 247 nm and the O peak at 777 nm. For the organic elements, a decay of signal for organic rich samples can be frequently seen. This is because the laser serves to pyrolyse some of the material surrounding the location of the laser spot, such that there is then less organics in the nearby material, which is observed on the next shot of the laser. However, the exact behavior may change depending on surface contamination and the composition of the inorganic matrix.

More advanced methods may be applied for pre-processing the spectra instead of integrating the intensity of a peak and plotting its change as a function of shot number, such as using the actual peak and its distribution of intensity for analysis instead of simply integrating its intensity, or using multiple peaks for an element, or combining the peak or peaks of one or more elements, or potentially using a sub-spectra or simply the whole spectrum for analysis.

The entire LIBS spectra can be used for the mineralogical or geochemistry analysis. One or more individual peaks in the LIBS spectra can be used for the mineralogical or geochemistry analysis, one or more sub-sections of the LIBS spectra, the intensity decay of peaks can be used for analysis of mineralogical or geochemistry properties. The intensity increase of peaks can be used for analysis of mineralogical or geochemistry properties. The raw data can be used for the analysis. The data can be pre-treated before analysis, such as applying an exponential fitting, bi-exponential fitting, multiple-exponential fitting, inverse Laplace transform, Gaussian decay fitting, or other analysis or filter. Combinations of these may be used.

Figure 9:
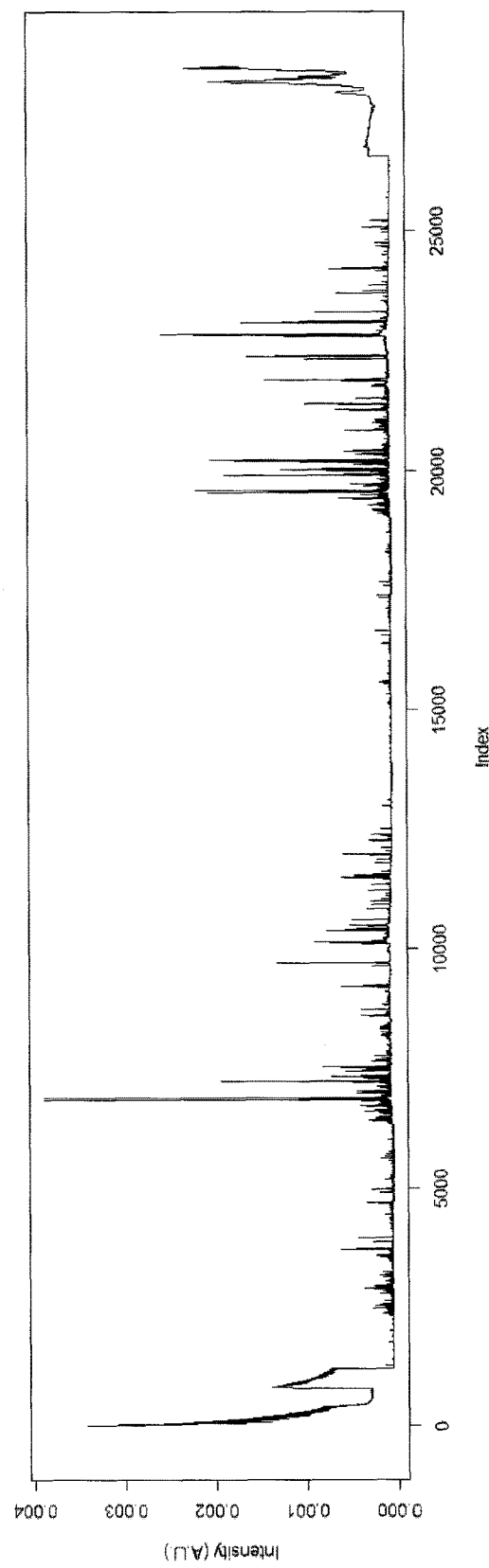
FIG. 9 shows an example of a sample data where the LIBS and FTIR data have been combined according to an example of the present application.
Figure 10:
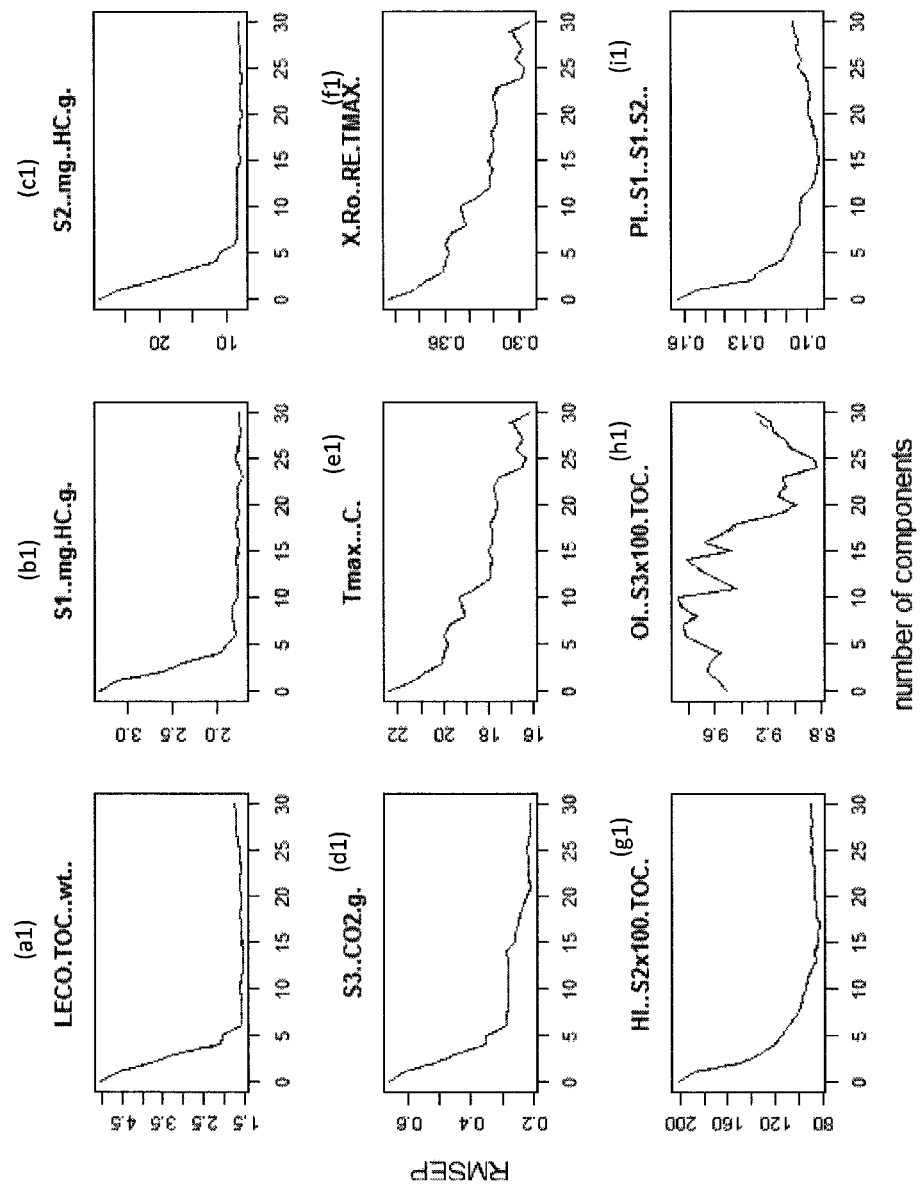
FIG. 10 shows the root mean square error of prediction for the models from combined LIBS-FTIR data compared to standard measurement techniques according to an example of the present application.
Figure 10:
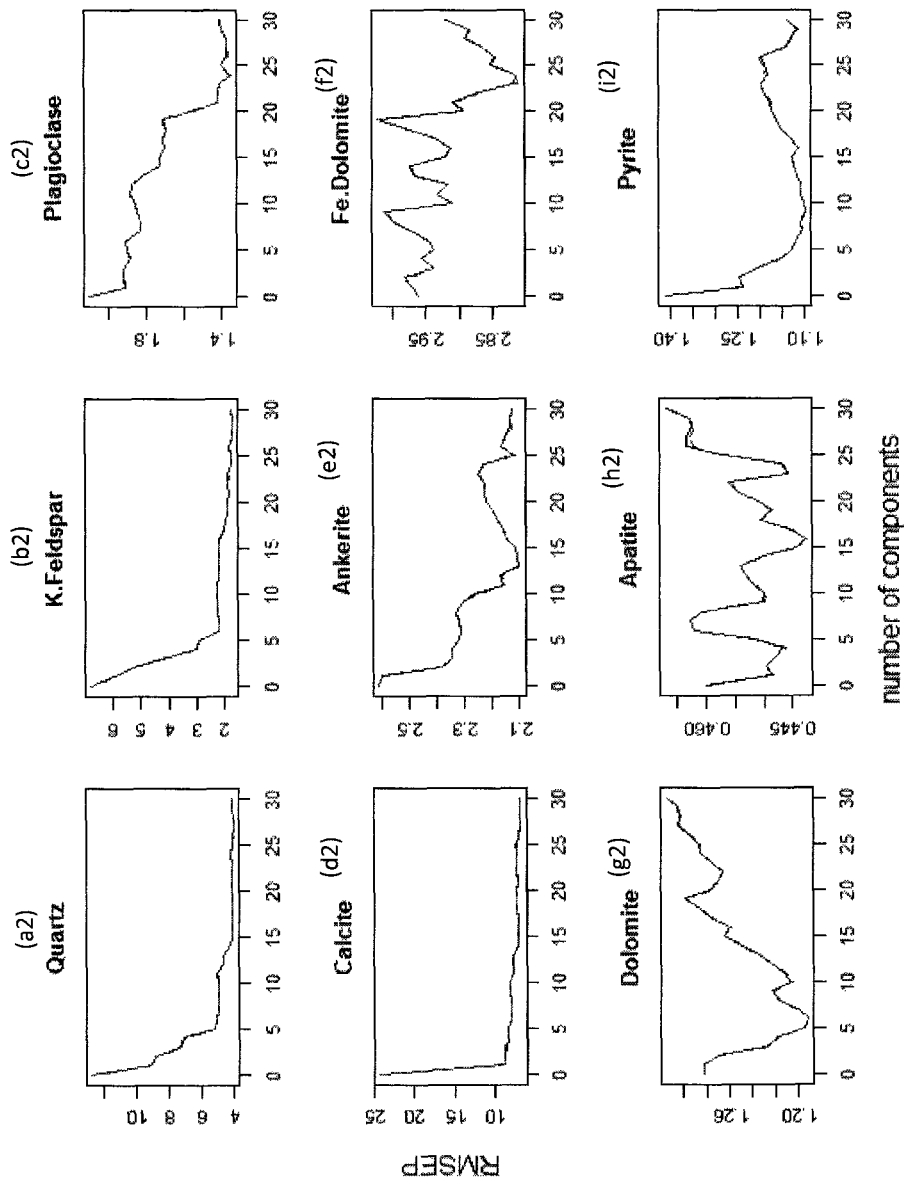
Figure 10:
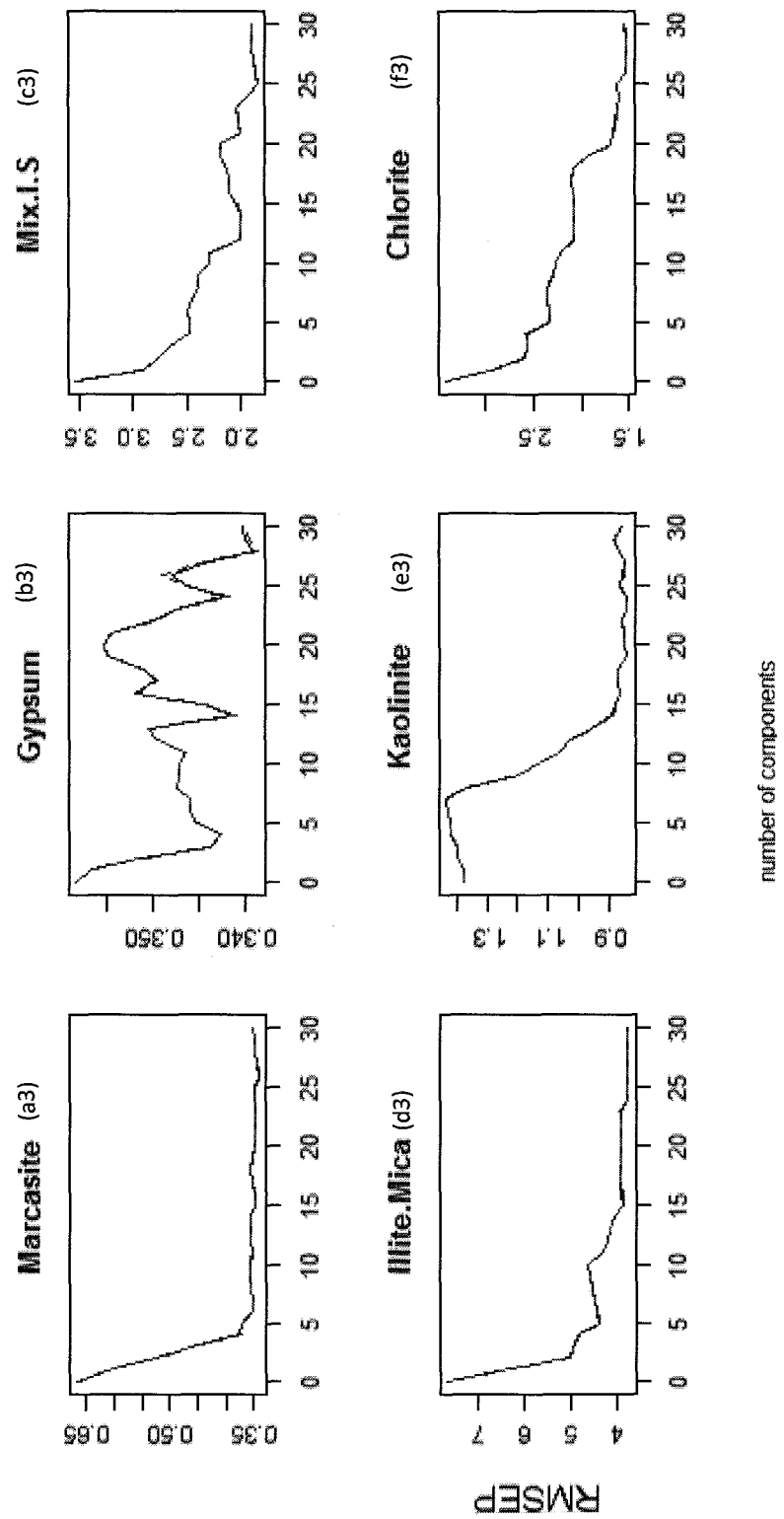
Figure 11:
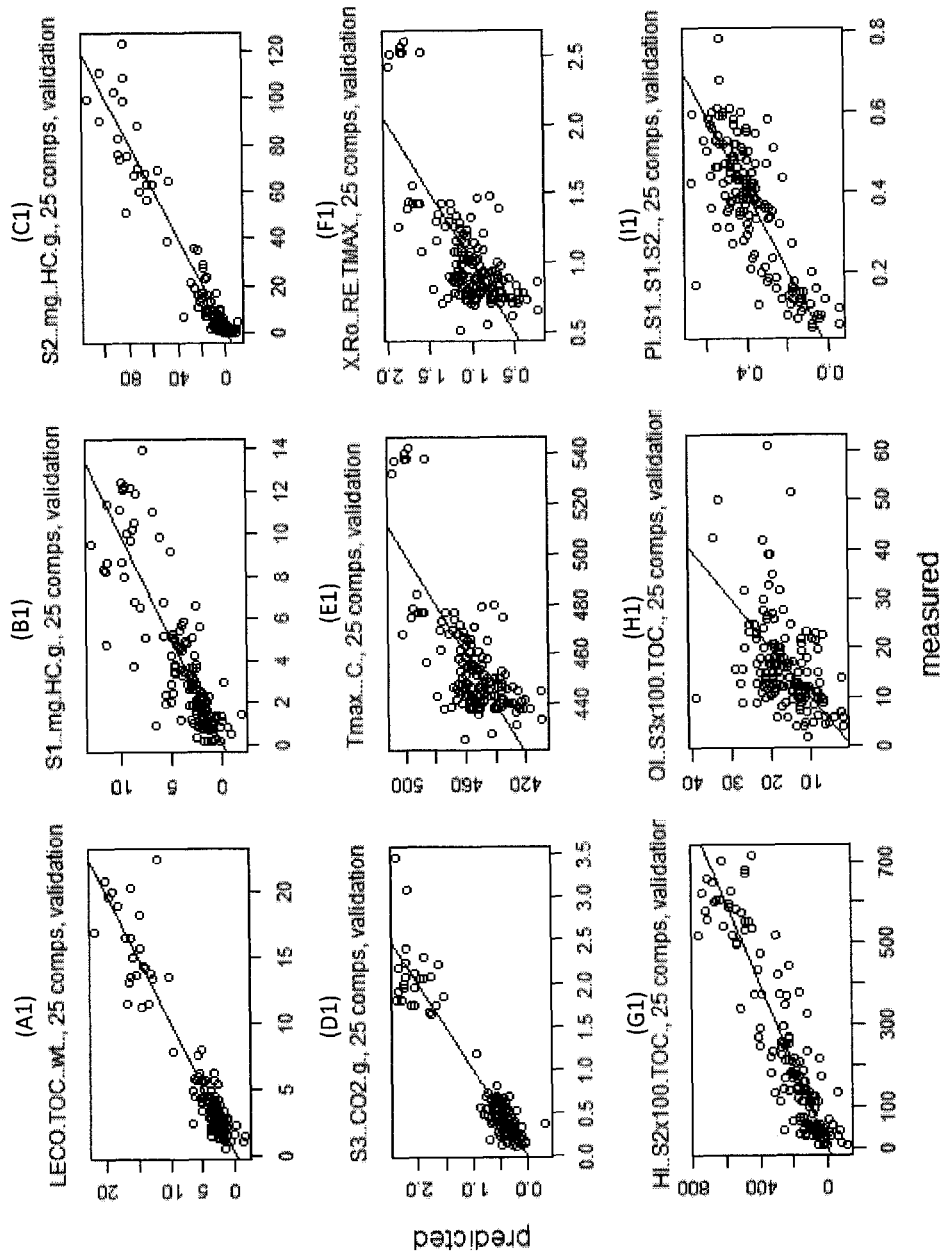
FIG. 11 shows the predicted mineralogy and geochemistry values from the combined LIBS-FTIR analysed by partial least squares analysis compared to the measured values from XRD, LECO TOC (carbon analyzer–total organic content), and Rock Eval™ according to an example of the present application.
Figure 11:
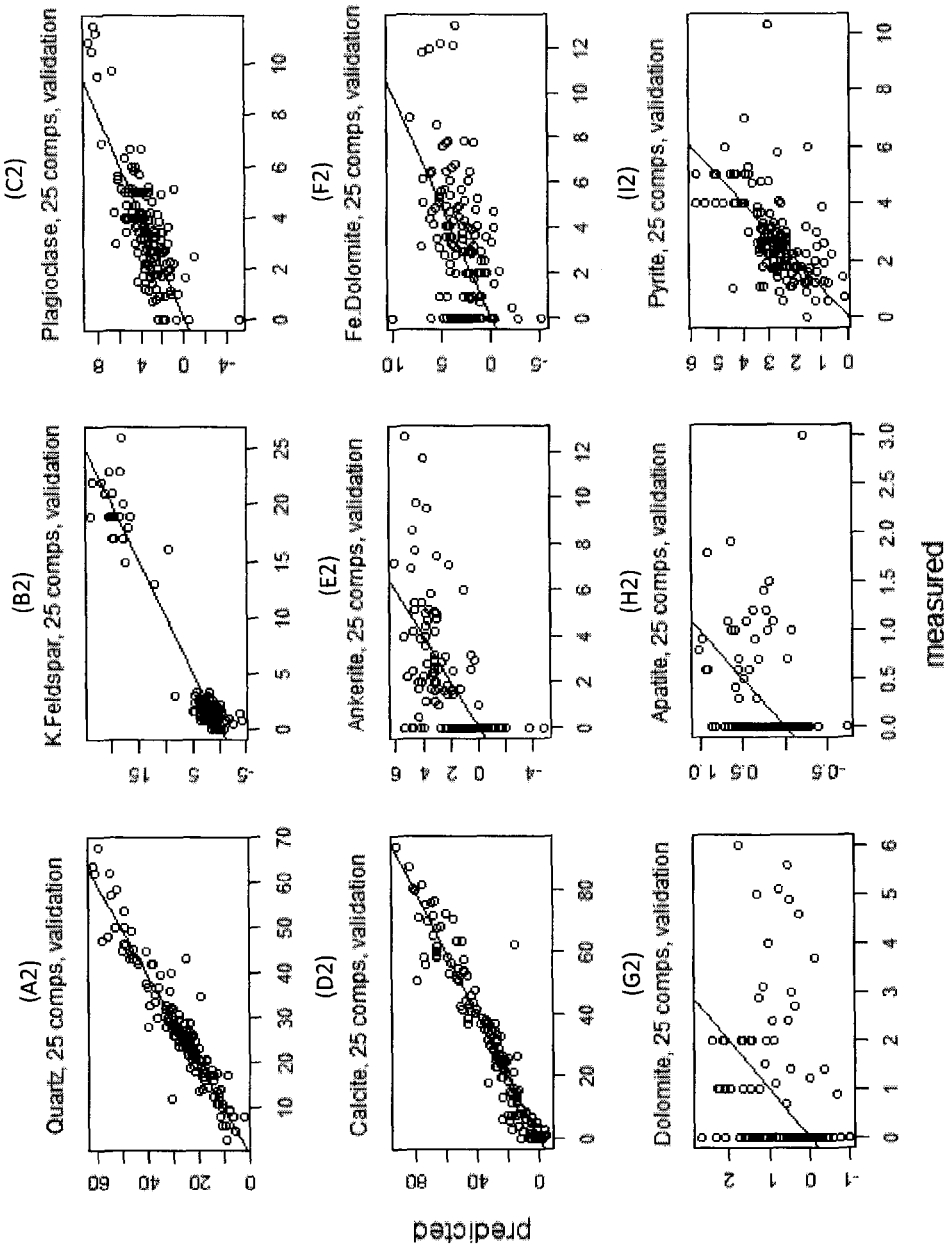
Figure 11:
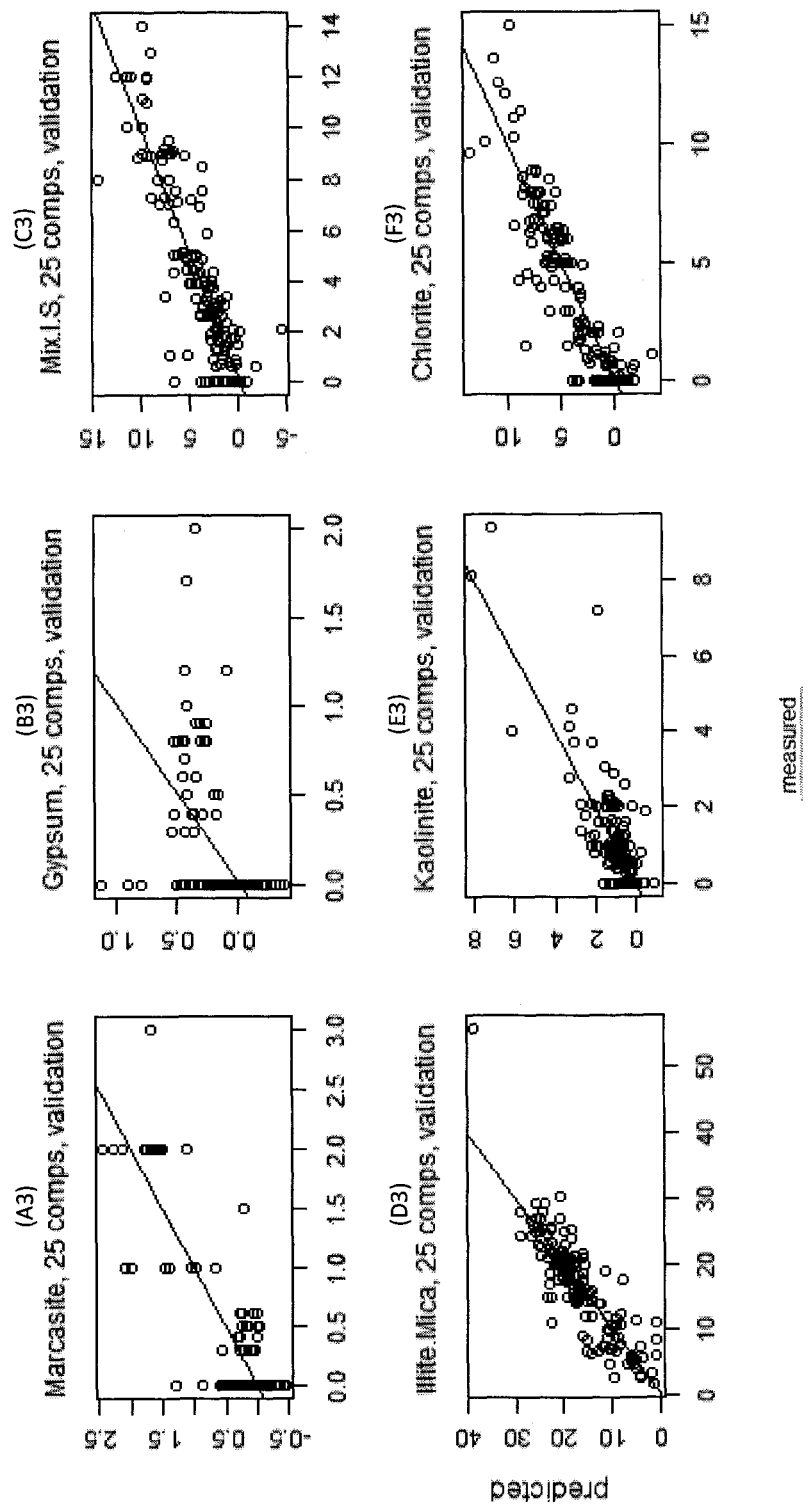

As an approach that can be used here, the individual intensity vectors for H, C and O (each of length 400) from LIBS are combined together into one long vector (length 1200) for each sample. This vector is then combined with a LIBS spectrum from the start of measurement, which includes both the organic and inorganic constituents, and a LIBS spectrum from the end of measurement, which contains mostly or only inorganic constituents, to produce a vector of length 26582. The long vector of each sample is then combined into a matrix of all the samples (149 by 26,582). The LIBS data is then concatenated with the matrix of FTIR measurements (149 by 1880) to produce one large combined matrix of the two measurements (149 by 28462). FIG. 9 shows an example of a sample data where the LIBS and FTIR data have been combined. Once the pre-processed spectra have been created, analysis can be performed on the data. A partial least square analysis can be then used to correlate the data to geochemical properties. The partial least squares works by trying to correlate the highest variance in the data with the highest variance in the property to be predicted, in our case things like quartz content, thermal maturity or bitumen content. A very good predictive value is seen for many geochemical parameters such as TOC, S1, S2, Ro and S3 and many minerals, such as illustrated in FIGS. 10-11. FIG. 10 shows the root mean square error of prediction (RMSEP) for the models from combined LIBS-FTIR data compared to standard measurement techniques. FIG. 10 includes figures a1-i1, a2-i2, and a3-f3. FIG. 11 shows the predicted mineralogy and geochemistry values from the combined LIBS-FTIR analysed by partial least squares analysis compared to the measured values from XRD, LECO TOC (carbon analyzer–total organic content), and Rock Eval™. FIG. 11 includes figures A1-I1, A2-I2, and A3-F3.

TOC, S1, S2, and S3 have been described hereinabove. With regard to the parameter Ro, vitrinite is found in many kerogens, and reflectivity can be measured by a microscope equipped with an oil-immersion objective lens and photometer. Vitrinite reflectance measures can represent the percentage of light reflected in oil, designated as Ro. Ro values can be indicators of thermal maturity, and can vary with the type of organic matter. For example, going from high Ro values to lower Ro values, the higher values may relate to dry gas and progressively lower values can relate to gas with a tendency toward oil generation, then wet gas, then predominantly oil, and lastly immature kerogen at the lowest values.

Other methods may be used to analyse the vibrational spectroscopy and LIBS data such as simple univariate analysis, multivariate analysis including but not limited to: principle component analysis, principle component regression, multiple linear regression, non-negative linear regression, cluster analysis, neural nets, self-organising maps, metaheuristic procedures (e.g. particle swarm optimization, genetic algorithms, etc.) and CAR (clustering assisted regression) analysis. Manual evaluation (i.e., looking at the spectra and making a judgment call) also may be used.

In addition, ratios between elements can be created by dividing the intensity vector for one element by another, for example H/C by dividing the H intensity vector by the C intensity vector. These change with shot number as well, though the intensity appears to be different depending on kerogen type. Using this procedure, the H/C and H/O ratios can be obtained. The H/C and H/O ratios are used to provide information on kerogen type (similar to a Van Krevelen diagram) and possibly information regarding thermal maturity or organic matter type or quality. Combining the LIBS data with FTIR can help improve predictions by providing additional information regarding the total organic content of the sample.

The inventive method can use these ratios of lighter elements, e.g., ratios using amounts of elements having an atomic weight of about 12 or lower that can be acquired with the LIBS-based method of the present invention, to great benefit.

Univariate analysis or multivariate analysis can be used to correlate the LIBS and vibrational spectral data to determined values for H/C ratio, H/O ratio, hydrogen index, programmed pyrolysis, thermal maturity property (e.g., thermal maturity, kinetic analysis), kerogen and bitumen content/discrimination, kerogen type, hydrocarbon content, hydrocarbon type, or any combinations thereof. Though H/C ratio and H/O ratio are used in these examples, the indicated univariate or multivariate analysis used in the method of the present invention also can be applied to other elemental ratios, and the indicated univariate or multivariate analysis can be applied to trace elemental content of the organic matter (e.g., sulfur (S), nitrogen (N), or other element), oxygen index, or any combinations thereof.

The present invention further relates to a method for determining geochemical information relating to kinetic analysis of a sample, comprising: a) making one or more vibrational spectral measurement; b) heating at least one sample by laser-induced pyrolysis, such as LIBS; c) monitoring the reaction rate, such as a value of the Arrhenius equation rate constant k, of at least one sample comprising at least one of: i) monitoring changes in amounts of elements associated with organic matter and hydrocarbons for a portion of at least one sample that is heated by the laser-induced pyrolysis, ii) collecting and analysing hydrocarbon species produced by pyrolysis of a portion of at least one sample from the laser-induced pyrolysis by a flame ion detector or gas chromatography-mass spectrometry (GC-MS), iii) monitoring the weight of at least one sample during the laser-induced pyrolysis of at least one sample, iv) monitoring the temperature of at least one sample and determining the amount of energy inputted into the portion of the sample by the laser during the laser-induced pyrolysis. The LIBS spectral data further can be used to perform a rapid kinetic analysis for determining how thermal maturation of one or more samples progresses depending on the energy input. For purposes herein, a reaction rate can refer to a generation rate for hydrocarbons from thermally-induced decomposition of kerogen in the sample, e.g., a hydrocarbon generation rate. In evaluating generation rates using kinetics analysis, the quantity, types, and rate at which hydrocarbons are generated from kerogen given particular heating conditions can be estimated in addition to determining what type and quantity of hydrocarbons the kerogen may already have produced. Kinetic analysis can be used to help understand the conversion process of organic matter from kerogen into products like thermobitumen, oil, gas and pyrobitumen. This can be used to help understand what petroleum products may have been produced by source rocks and reservoir rocks, such as for the case of tight oil and gas shales, and for the case of oil shale, what petroleum products may be produced in the future, and at what generation rates. Kerogen maturation can be considered to be tied to chemical reaction rates. Many kinetic formulations assume that kerogen directly converts to oil and gas hydrocarbons, or other formulations assume that kerogen converts to hydrocarbons via bitumen intermediate. Kinetic models can use the Arrhenius equation, which is given by equation (1): $k=Ae^{-Ea/RT}$. In the indicated Arrhenius equation, k is the rate constant of the chemical reaction, such as the reaction rate constant for loss of the reacting (decomposing) species of kerogen in the transformation of kerogen to hydrocarbons, which can be expressed as the change in the molar mass of the reactant with respect to time. A is the pre-exponential or frequency factor, which describes the number of potential elementary reactions per unit time (e.g., in units of $min^{-1}$). $E_a$ is the activation energy that describes the energy barrier that must be exceeded in order for a reaction to occur (in energy/mole, e.g., kiloJoule/mole). R is the gas constant (e.g., 0.008314 kJ/° K-mole), and T is the absolute temperature (° K). If kinetic analysis is performed by running programmed pyrolysis measurements, the temperature of the oven is known, the quantity of produced organic products monitored and can be used to obtain the distribution of $E_a$ value for a sample. When determining $E_a$ from data obtained using a pyrolysis oven in programmed pyrolysis measurements, a challenge is in determining the value of A. Typically several programmed pyrolysis measurements can be performed with different heating rates for purposes of solving for the value of A. In kinetic analysis that uses a multiple-heating ramp open-system pyrolysis strategy, kinetic analyses begins with pyrolysis of source rock samples in an oven using two, three, or more different heating rates (e.g., different ° C./min heating rates). When the reaction in question is first order and occurs under isothermal conditions, then activation energies ($E_a$) and frequency factors (A) may be obtained from a plot of the natural logarithm of the reaction rate (ln k) versus the inverse of the absolute temperature (1/T), where k is the reaction rate (mass/time) and T is the temperature (T in ° K). Activation energies and frequency factors also may be found using non-isothermal experiments as long as the temperature varies at a constant rate. An approximate solution for the Arrhenius equation under those conditions can use the Kissinger method or other approaches. E.g., S. H. Nordeng, "Evaluating Source Rock Maturity Using Multi-Sample Kinetic Parameters . . . ," Geol. Investig. No. 164, North Dak. Geol. Survey, 2013, pp. 1-19. In some cases, A is either fixed or assigned from a priori knowledge such that only one heating rate is necessary in a one-run, open-system pyrolysis experiment ("single ramp" pyrolysis). The present invention can include a method for determining kinetic properties such as reaction rates or activation energies for a sample that does not require heating of an entire sample in a pyrolysis oven and can provide reliable information on how a sample has and will thermally mature.

Instead of heating an entire sample in an oven to generate data for kinetic modeling, in the present invention a laser, such as applied using LIBS, can be used to pyrolyse the sample at a single or multiple selected locations, such as discrete spots on the sample. Then at least one location of the sample can be subjected to a plurality of successive measurement shots of laser light with each measurement shot at least partly vaporising and ionising the sample to cause spectral emission, which is detected after each measurement shot with at least one spectral detector. The spectral data acquired from the spectrum detector can be preprocessed, such as by the indicated univariate analysis or multivariate analysis. The acquired spectral data, raw or preprocessed, can be used in a kinetic analysis of the sample. A laser, such as applied using LIBS, can be used as the source of heat that pyrolyzes the sample, and k, $E_a$ and/or other kinetic property data can be determined for the laser-heated portion of the sample by one or several different strategies from the spectral data acquired from using LIBS as indicated. In this respect, k, $E_a$ and/or other kinetic property data can be determined from the indicated spectral data obtained during laser heating of a portion of the sample based on changes in amounts of elements associated with organic matter and hydrocarbons, e.g., by monitoring the increase or decrease in elements associated with organic matter and hydrocarbons. In another respect, k, $E_a$ and/or other kinetic property data can be determined from spectral data obtained during the laser heating of a portion of the sample by collection and analysis of the produced hydrocarbon species from LIBS further by a flame ion detector or gas chromatography-mass spectrometry (GC-MS) or by monitoring weight of the sample during LIBS. Alternatively, as the amount of energy inputted into the system by the laser is known, by monitoring the temperature of the sample, k can be calculated for a portion of the sample that is heated by LIBS. Combinations of these strategies may be used. In these respects, a single or multiple LIBS measurements can be performed which can have the same or different settings of the laser power, repetition rate or spot size. As indicated, a LIBS measurement can comprise successive shots of laser light with each measurement shot at least partly vaporising and ionising the sample to cause spectral emission, which is detected after each measurement shot. Temperature can be assumed based on prior information, or calculated through the intensity of the LIBS peaks in the spectra, or by monitoring the sample through a device such as an infrared (IR) camera. A combination of monitoring the inputted energy to the system, the sample temperature, produced products, and sample composition from vibrational spectroscopy can provide an understanding of the chemical kinetics of the organic matter maturation, such as the reaction rate or distribution of activation energies. If an IR camera is used in determining the sample temperature resulting from the laser treatment, in addition to understanding the kinetics analysis of the organic matter, the heat transfer properties of the shale can be observed by monitoring the temperature of the sample after laser shots and how the temperature changes around the laser spot as a function of time. The generated kinetic property data by the inventive method can be locationally-mapped across a surface of the sample, and/or for different depths of the same sample (or different sample).

Though not limited thereto, a LIBS system which may be adapted for implementing a method of the present invention can have a laser capable of causing vaporisation and ionisation of a part of the geological sample and a spectral detector with a wide spectral range and a high sensitivity, fast response rate, time gated detector. These components can be coupled to a computer which can rapidly process and interpret the acquired data.

Suitable lasers can include solid state lasers such as the 1064 nm Nd:YAG laser, harmonic wavelengths of the Nd:YAG laser, e.g., 532 nm, 355 nm, and 266 nm; gas lasers such as excimer lasers, e.g., 308 nm XeCl, or 248 nm KrF excimer lasers; carbon dioxide lasers; liquid lasers such as dye lasers; or any wavelength/frequency shifting, harmonic generation or combinations of the above. Lasers other than those specifically mentioned may also be used.

Each of the plurality of detectors can comprise a spectrometer adjusted to a part of the spectral region. Each of the spectrometers, for example, may have a CCD detector associated with the spectrometer. The CCD detector may pass information on the spectral region to a data acquisition card or a data file in a computer or memory space. This data may then be analysed to determine the presence of one or more elements in the material and to determine the amount or concentration of the element in the geological material in manners described herein.

Spectrometer types suitable for use in the present invention can include grating and prism spectrographs; interferometers, such as etalon and scanning interferometer types; and filters, including coloured glass or interference filter types which allow transmission or reflection of a portion of the spectrum. Each of the plurality of spectral detectors can comprise a spectrometer adjusted to detect a contiguous part of the spectral region. Detectors which can be used in the present invention include the above-indicated CCD's (charged-coupled detectors) or other detectors such photodiode arrays, vidicons, photomultiplier tubes and photodiodes. A multi-channel broadband spectrometer ($\lambda$ range of 190-950), Echelle spectrometer with iCCD detector may be used ($\lambda$ range of 200-900), or other spectral detectors may be used. A person skilled in the art can readily appreciate which detector(s) can be used.

The system or apparatus of the present invention can further comprise a controller for controlling the firing of the laser and for controlling and synchronising operation of the plurality of detectors therewith. That is, the controller may include a timing circuit to fire the laser at specified times and to operate the detectors at other specified times. The controller, for example, can simultaneously turn on a plurality of spectrometers at a short time after the laser is fired, and the plural spectrometers being otherwise turned off. In place of the timing circuit, the controller may comprise control software to control operation of the laser and the detection means. The controller can operate under the direction of control software to send a control signal which causes the laser to emit a pulse of laser light and to send a control signal to each of the plurality of spectral detectors which turns on the spectral detectors. In such manners, the controller can be used to synchronise operation of each of the plurality of detectors such that the plurality of detectors simultaneously detect spectral emissions from the material.

The systems or apparatus can also include one or more optical systems to focus the laser light on the geological material and to focus the spectral emissions on the plurality of detectors. The one or more optical systems may include one or more lenses, optical fibre, prisms, beam splitters or other optical components. Although suitable optical systems are typically needed, the specific design of the optical system does not form part of the invention and a person skilled in the art should be able to design a variety of different suitable optical systems.

Figure 12:
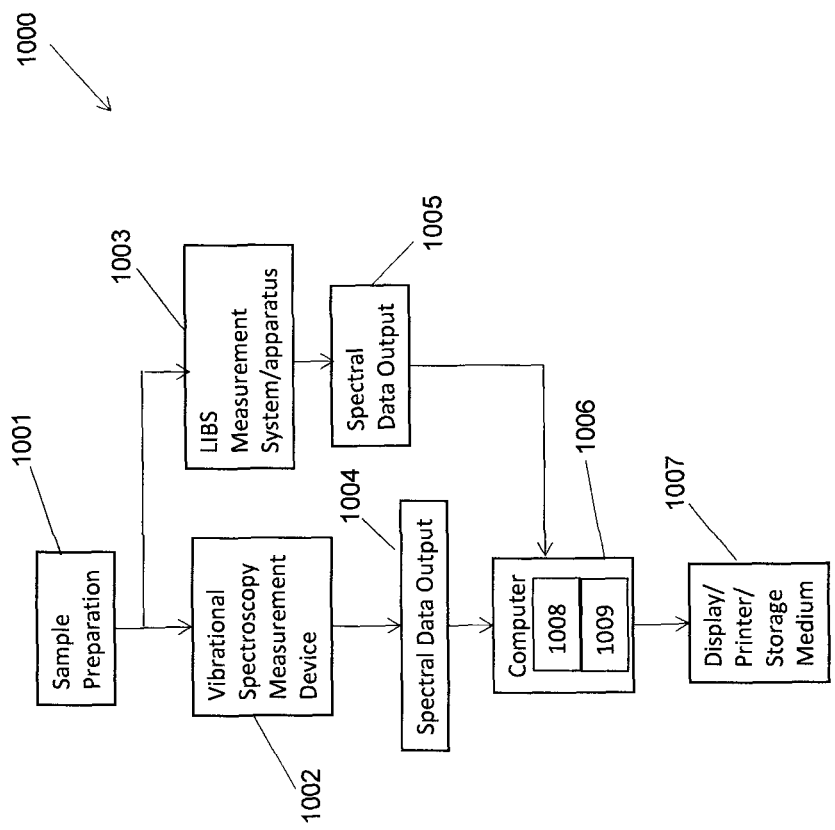
FIG. 12 shows a system according to an example of the present application.

The present invention also relates to a system for determining mineralogy or geochemistry of a sample of petroleum source or reservoir rock, such as according to the processes described herein. As illustrated in FIG. 12, for example, the system 1000 can include a sample preparation station 1001, at least one vibrational spectroscopy measurement device 1002 (e.g., a FTIR spectrometer), a LIBS measurement system or apparatus 1003 (e.g., such as shown in more detail in FIG. 6). Spectral data outputs 1004 and 1005 obtained using these devices are received by one or more computer systems 1006. The one or more computer systems 1006 can be provided for processing of spectral data obtained from the vibrational spectroscopy measurement device 1002 and the LIBS measurement system 1003 according to methods of the present invention, and to output the results to at least one output device 1007 to display, print, or store results, or any combinations thereof, of the spectral data and results of computations based thereon using a method of the present application. The computer can comprise at least one memory device 1008 and at least one processor 1009, wherein the memory can include a stored program comprising a set of instructions performed by the processor for executing process steps of the present invention that involve spectral data analysis and computations based thereon. The computer programs used for spectral data analysis and the computations can be stored, as a program product, on at least one non-transitory computer usable storage medium (e.g. a hard disk, a flash memory device, a compact disc, a magnetic tape/disk, or other media) associated with at least one processor (e.g., a CPU) which is adapted to run the programs, or may be stored on an external non-transitory computer usable storage medium which is accessible to the computer processor. The indicated system or apparatus of the present invention may be suitable for analysing material in a laboratory in a building, or in-the-field, such as in a mobile transport vehicle or mechanism on the ground or underground.

As indicated, the mineralogical or geochemistry parameters which can be obtained by a method of the present invention can be used as input into a process for determining spatially resolved geochemistry or mineralogy of a geological material and/or as integrated with other kinds of mineralogical or geochemical parameter data, for use in characterising or modeling of the sample and/or geological reservoir from which the sample was obtained. For example, the spectral data can be integrated into two or three dimensional models created from spatial imaging, to generate spatially resolved mineralogical or geochemical information on the sample. Appropriate spatial mineralogical or geochemistry information in the 2D or 3D models can be determined through image segmentation, assigned manually, determined by capillary pressure simulation or measurements, or determined from previously spatially resolved spectral measurements. Modes of spatial information acquisition on geological samples are known in the industry, including, e.g., X-ray CT, NMR, SEM, FIB-SEM, neutron scattering, thin sections, and high resolution photography. These can be adapted for use in a process of obtaining spatially resolved mineralogical or geochemical information with integration of the spatial information with mineralogical or geochemistry parameter information obtained using the method of the present invention.

The present invention includes the following aspects/embodiments/features in any order and/or in any combination:

1. The present invention relates to a method for determining mineralogy or geochemistry of a sample of a petroleum source or reservoir rock, comprising:
   a) obtaining one set of spectral data comprising vibrational spectral data on at least one sample of a petroleum source or reservoir rock;
   b) obtaining another set of spectral data comprising LIBS spectral information on at least one sample of a petroleum source or reservoir rock;
   c) obtaining at least one of mineralogical information and geochemical information on the at least one sample using the two sets of spectral data, wherein the sample in a) and the sample in b) are the same or are different but have the same or similar composition and structure.

2. The method of any preceding or following embodiment/feature/aspect, wherein the vibrational spectral data on the sample is generated by FTIR, FTIR microscopy, Raman spectroscopy, hyperspectral imaging, or any combinations thereof.

3. The method of any preceding or following embodiment/feature/aspect, wherein the vibrational spectral data on the at least one sample is generated by FTIR or FTIR microscopy.

4. The method of any preceding or following embodiment/feature/aspect, wherein the vibrational spectral data on the at least one sample is generated using vibrational spectroscopy using a polychromatic light source.

5. The method of any preceding or following embodiment/feature/aspect, wherein a) comprises directing a light beam containing multiple frequencies of light onto the at least one sample, and determining light absorption for each frequency (wavelength).

6. The method of any preceding or following embodiment/feature/aspect, wherein the LIBS information is obtained by a plurality of successive measurement shots of laser light with each measurement shot at least partly vaporising and ionising the sample to cause spectral emission, and detecting the spectral emission after each measurement shot with at least one spectrum detector.

7. The method of any preceding or following embodiment/feature/aspect, wherein (i) the sample undergoes vibrational spectral measurement and the LIBS measurement in the same setup, or (ii) the sample undergoes vibrational spectral measurement and then is transferred to a second setup for LIBS measurement, or (iii) the sample undergoes LIBS measurement and is then transferred to a second equipment for vibrational spectral measurement, or (iv) the sample undergoes vibrational spectral measurement and then is transferred to a second setup for LIBS measurement and then returned to the original or another setup for a second vibrational spectral measurement, or (v) the sample undergoes vibrational spectral measurement and LIBS measurement and one or more intermediate measurements between the two types of measurements, or (vi) the LIBS and vibrational spectral measurements are performed independently in two different setups, wherein the vibrational spectral and LIBS measurements are performed on the same sample, different portions of the same sample, or two or more different samples of similar composition and structure.

8. The method of any preceding or following embodiment/feature/aspect, wherein the sample undergoes vibrational spectral measurement, then is transferred to a second setup for LIBS measurement, and then returned to the original or another setup for a second vibrational spectral measurement, wherein the second vibrational spectral measurement is performed on a laser spot produced on the sample from the LIBS measurement.

9. The method of any preceding or following embodiment/feature/aspect, wherein the geochemical information is obtained with determined values for H/C ratio, H/O ratio, C/O ratio, HI index, OI index, isotope determination, trace element determination, organic matter typing, thermal maturity, kerogen/bitumen discrimination, kerogen quality, Rock Eval parameters or any combinations thereof.

10. The method of any preceding or following embodiment/feature/aspect, wherein the geochemical information is obtained with determined values for organic matter typing, organic matter elemental content, thermal maturity of organic content, kerogen/bitumen discrimination, or any combinations thereof.

11. The method of any preceding or following embodiment/feature/aspect, wherein spatially resolved mineralogical or geochemical information is provided to a 2D or 3D model that is determined through image segmentation, assigned manually, determined by capillary pressure simulation or measurements, or determined from previously spatially resolved spectral measurements.

12. The method of any preceding or following embodiment/feature/aspect where the vibrational spectroscopy data and the LIBS data is combined for data analysis comprising at least one of
   1) concatenation of the data, turning the two or more separate data matrices into a single matrix that contains both the vibrational spectroscopy and LIBS data, which can then be used in the analysis methods to predict mineralogy and geological parameters;
   2) inputting the one or more vibrational spectroscopy measurements and LIBS data separately into the analysis method, such as the Multi-Block or N-PLS method, for prediction of mineralogical and geochemistry parameters;
   3) combining the data by initially analyzing the vibrational spectroscopy data for initial predictions or constraints on mineralogical or geochemical parameters that are then inputted with the LIBS data for subsequent analysis, wherein the initial predictions or constraints from the vibrational spectroscopy may either be inputted as a separate matrix into the second analysis method or may be concatenated with the LIBS data to create a single, large matrix;

4) combining the data by initially analyzing the LIBS data to get out initial predictions or constraints on mineralogical or geochemical parameters that are then inputted with the vibrational spectroscopy data for subsequent analysis, wherein the initial predictions or constraints from the LIBS may either be inputted as a separate matrix into the second analysis method or may be concatenated with the vibrational data to create a single, large matrix.

13. The method of any preceding or following embodiment/feature/aspect, wherein the geochemistry parameter is obtained wherein partial least square analysis, or manual or uni or multivariate analysis or cluster analysis or self-organising maps or neural nets or metaheuristic procedures is used to correlate the collected first and second sets of spectral data, raw or pre-processed, to determine values for H/C ratio, H/O ratio, trace elemental content of the organic matter for at least one of S and N or other elements, hydrogen index, oxygen index, programmed pyrolysis, thermal maturity property, kerogen and bitumen content/discrimination, kerogen type, hydrocarbon content, hydrocarbon type, or any combinations thereof.

14. The present invention further relates to a method for determining mineralogy or geochemistry of a sample of a petroleum source or reservoir rock, comprising:
    a) crushing a sample of a petroleum source or reservoir rock to form a powder thereof;
    b) mixing the powder to provide a homogenized sample;
    c) obtaining one set of spectral data comprising vibrational spectral data on one portion of the homogenized sample;
    d) pressing another portion of the homogenized sample to provide a pelletized sample;
    e) obtaining another set of spectral data comprising LIBS spectral information on the pelletized sample;
    f) obtaining at least one of mineralogical information and geochemical information on the sample using the two sets of spectral data.

15. The present invention further relates to a method for determining geochemistry of a sample of a petroleum source or reservoir rock sample, comprising:
    a) obtaining one set of spectral data comprising vibrational spectral data on at least one sample of a petroleum source or reservoir rock;
    b) obtaining another set of spectral data comprising spectral information generated by laser induced pyrolysis on at least one sample of a petroleum source or reservoir rock;
    c) obtaining geochemical information on the at least one sample using the two sets of spectral data, wherein the geochemical information comprises kinetic analysis for at least one sample, wherein the sample in a) and the sample in b) are the same or are different but have the same or similar composition and structure;
    d) obtaining spatial information on the at least one sample;
    e) determining spatially resolved geochemical information for the at least one sample using the geochemical information and the spatial information.

16. The present invention further relates to a method for performing kinetic analysis as geochemical information of a sample of a petroleum source or reservoir rock, comprising:
    a) making a vibrational spectroscopy measurement on at least one sample of a petroleum source or reservoir rock;
    b) heating at least one sample of a petroleum source or reservoir rock by laser-induced pyrolysis, wherein the sample in a) and the sample in b) are the same or are different but have the same or similar composition and structure;
    c) determining a reaction rate, such as a value of the Arrhenius equation rate constant k, of the at least one sample of b) comprising at least one of:
        i) determining changes in amounts of elements associated with organic matter and hydrocarbons for a portion of at least one sample that is heated by the laser-induced pyrolysis,
        ii) collecting and analysing hydrocarbon species produced by pyrolysis of a portion of at least one sample from the laser-induced pyrolysis by a flame ion detector or gas chromatography-mass spectrometry (GC-MS),
        iii) monitoring weight of at least one sample during the laser-induced pyrolysis of at least one sample,
        iv) monitoring the temperature of at least one sample and determining the amount of energy inputted into the portion of the sample by the laser during the laser-induced pyrolysis, or using any combination of i), ii), iii), and iv), such as ii) and/or iii) in conjunction with either i) or iv).

17. The method of any preceding or following embodiment/feature/aspect, wherein a prefactor in the Arrhenius equation is inputted based on a priori knowledge or solved for based on measurements performed on two or more different heating rates of the sample.

18. The method of any preceding or following embodiment/feature/aspect, wherein the different heating rates are obtained by one or more of different laser power, laser spot size or laser shot rate, or any combination thereof.

19. The method of any preceding or following embodiment/feature/aspect, wherein the kinetic analysis by LIBS and vibrational spectroscopy is used to either solve for the activation energy distribution in the sample or the reaction rates given a known input of energy.

20. The present invention further relates to a system for determining mineralogy or geochemistry of a sample, comprising i) a vibrational spectral data acquisition device for obtaining vibrational spectral data on at least one sample; ii) a LIBS spectral data acquisition device for obtaining LIBS spectral information on at least one sample; iii) a spatial information acquisition device for obtaining spatial information on at least one sample, wherein the vibrational spectral data acquisition device, the LIBS spectral data acquisition device, and the spatial information acquisition device are the same device or different devices, and wherein the sample used in i), the sample used in ii), and the sample used in iii) are the same or are different but have the same or similar composition and structure; iv) one or more computer systems comprising at least one processor and a non-transitory computer-readable medium including a stored program comprising a set of instructions performed by the processor for carrying out steps to obtain mineralogical or geochemical information on the sample or samples used in i) and ii) using the spectral data, and to determine spatially resolved mineralogical or geochemical information for the sample or samples used in i), ii), and iii) using the mineralogical or geochemical information and the spatial information; and v) at least one device to display, print, and/or store as a non-transitory storage medium, results of the computations.

The present invention can include any combination of these various features or embodiments above and/or below as set forth in sentences and/or paragraphs. Any combination of disclosed features herein is considered part of the present invention and no limitation is intended with respect to combinable features.

Applicant specifically incorporates the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

The invention claimed is:

1. A method for determining mineralogy or geochemistry of a sample of a petroleum source or reservoir rock, comprising:
   a) obtaining one set of spectral data comprising vibrational spectral data on the sample;
   b) obtaining another set of spectral data comprising LIBS spectral information on the sample, or a second sample of the petroleum source or reservoir rock that has a similar composition and structure;
   c) obtaining mineralogical information or geochemical information on the sample using the two sets of spectral data
   d) obtaining spatial information on the sample, using a vibrational spectroscopy measurement device or a LIBS measurement system; and
   e) determining spatially resolved geochemical information for the sample using the mineralogical information or geochemical information and the spatial information.

2. The method of claim 1, wherein the vibrational spectral data on the sample is generated by FTIR, FTIR microscopy, Raman spectroscopy, hyperspectral imaging, or any combinations thereof.

3. The method of claim 1, wherein the vibrational spectral data on the second sample is generated by FTIR or FTIR microscopy.

4. The method of claim 1, wherein the vibrational spectral data on the sample or the second sample is generated using vibrational spectroscopy using a polychromatic light source.

5. The method of claim 1, wherein a) comprises directing a light beam containing multiple frequencies of light onto the sample, and determining light absorption for each frequency (wavelength).

6. The method of claim 1, wherein the LIBS information is obtained by a plurality of successive measurement shots of laser light with each measurement shot at least partly vaporising and ionising the sample to cause spectral emission, and detecting the spectral emission after each measurement shot with at least one spectrum detector.

7. The method of claim 1, wherein (i) the sample undergoes vibrational spectral measurement and the LIBS measurement in the same setup, or (ii) the sample undergoes vibrational spectral measurement and then is transferred to a second setup for LIBS measurement, or (iii) the sample undergoes LIBS measurement and is then transferred to a second equipment for vibrational spectral measurement, or (iv) the sample undergoes vibrational spectral measurement and then is transferred to a second setup for LIBS measurement and then returned to the original or another setup for a second vibrational spectral measurement, or (v) the sample undergoes vibrational spectral measurement and LIBS measurement and one or more intermediate measurements between the two types of measurements, or (vi) the LIBS and vibrational spectral measurements are performed independently in two different setups, wherein the vibrational spectral and LIBS measurements are performed on the same sample, different portions of the same sample, or two or more different samples of similar composition and structure.

8. The method of claim 1, wherein the sample undergoes vibrational spectral measurement, then is transferred to a second setup for LIBS measurement, and then returned to the original or another setup for a second vibrational spectral measurement, wherein the second vibrational spectral measurement is performed on a laser spot produced on the sample from the LIBS measurement.

9. The method of claim 1, wherein the geochemical information is obtained with determined values for H/C ratio, H/O ratio, C/O ratio, HI index, OI index, isotope determination, trace element determination, organic matter typing, thermal maturity, kerogen/bitumen discrimination, kerogen quality, Rock Eval parameters or any combinations thereof.

10. The method of claim 1, wherein the geochemical information is obtained with determined values for organic matter typing, organic matter elemental content, thermal maturity of organic content, kerogen/bitumen discrimination, or any combinations thereof.

11. The method of claim 1, wherein the spatially resolved mineralogical or geochemical information is provided to a 2D or 3D model that is determined through image segmentation, assigned manually, determined by capillary pressure simulation or measurements, or determined from previously spatially resolved spectral measurements.

12. The method of claim 1 where the vibrational spectroscopy data and the LIBS data is combined for data analysis comprising at least one of
   1) concatenation of the data, turning the two or more separate data matrices into a single matrix that contains both the vibrational spectroscopy and LIBS data, which can then be used in the analysis methods to predict mineralogy and geological parameters;
   2) inputting the one or more vibrational spectroscopy measurements and LIBS data separately into the analysis method, such as the Multi-Block or N-PLS method, for prediction of mineralogical and geochemistry parameters;
   3) combining the data by initially analyzing the vibrational spectroscopy data for initial predictions or constraints on mineralogical or geochemical parameters that are then inputted with the LIBS data for subsequent analysis, wherein the initial predictions or constraints from the vibrational spectroscopy may either be inputted as a separate matrix into the second analysis method or may be concatenated with the LIBS data to create a single, large matrix;

4) combining the data by initially analyzing the LIBS data to get out initial predictions or constraints on mineralogical or geochemical parameters that are then inputted with the vibrational spectroscopy data for subsequent analysis; wherein the initial predictions or constraints from the LIBS may either be inputted as a separate matrix into the second analysis method or may be concatenated with the vibrational data to create a single, large matrix.

13. The method of claim 1, wherein the mineralogy or geochemistry parameter is obtained wherein partial least square analysis, or manual or uni or multivariate analysis or cluster analysis or self-organising maps or neural nets or metaheuristic procedures is used to correlate the collected first and second sets of spectral data, raw or pre-processed, to determine values for H/C ratio, H/O ratio, trace elemental content of the organic matter for at least one of S and N or other elements, hydrogen index, oxygen index, programmed pyrolysis, thermal maturity property, kerogen and bitumen content/discrimination, kerogen type, hydrocarbon content, hydrocarbon type, or any combinations thereof.

14. A method for determining mineralogy or geochemistry of a sample of a petroleum source or reservoir rock, comprising:
  a) crushing a sample of a petroleum source or reservoir rock to form a powder thereof;
  b) mixing the powder to provide a homogenized sample;
  c) obtaining one set of spectral data comprising vibrational spectral data on one portion of the homogenized sample;
  d) pressing another portion of the homogenized sample to provide a pelletized sample;
  e) obtaining another set of spectral data comprising LIBS spectral information on the pelletized sample; and
  f) obtaining at least one of mineralogical information or geochemical information on the sample using the two sets of spectral data.

15. A system for determining mineralogy or geochemistry of a sample, comprising
  i) a vibrational spectral data acquisition device for obtaining vibrational spectral data on at least one sample;
  ii) a LIBS spectral data acquisition device for obtaining LIBS spectral information on at least one sample;
  iii) a spatial information acquisition device for obtaining spatial information on at least one sample, wherein the vibrational spectral data acquisition device, the LIBS spectral data acquisition device, and the spatial information acquisition device are the same device or different devices, and wherein the sample used in i), the sample used in ii), and the sample used in iii) are the same or are different but have the same or similar composition and structure;
  iv) one or more computer systems comprising at least one processor and a non-transitory computer-readable medium including a stored program comprising a set of instructions performed by the processor for carrying out steps to obtain mineralogy or geochemical information on the sample or samples used in i) and ii) using the spectral data, and to determine spatially resolved mineralogy or geochemical information for the sample or samples used in i), ii), and iii) using the mineralogy or geochemical information and the spatial information; and
  v) at least one device to display, print, and/or store as a non-transitory storage medium, results of the computations.

* * * * *